(12) United States Patent
Kiser et al.

(10) Patent No.: US 6,521,431 B1
(45) Date of Patent: Feb. 18, 2003

(54) BIODEGRADABLE CROSS-LINKERS HAVING A POLYACID CONNECTED TO REACTIVE GROUPS FOR CROSS-LINKING POLYMER FILAMENTS

(75) Inventors: Patrick F. Kiser, Durham, NC (US); Allen A. Thomas, Carlsbad, CA (US)

(73) Assignee: Access Pharmaceuticals, Inc., Dallas, TX (US)

( * ) Notice: Subject to any disclaimer, the term of this patent is extended or adjusted under 35 U.S.C. 154(b) by 0 days.

(21) Appl. No.: 09/338,404

(22) Filed: Jun. 22, 1999

(51) Int. Cl.[7] .................. C12N 11/02; C12N 11/00; A61K 9/14; C07K 17/00; C07K 17/02

(52) U.S. Cl. .................. 435/177; 424/484; 424/486; 424/489; 424/93.1; 424/93.7; 435/174; 435/178; 435/180; 435/395; 530/812; 530/813; 530/815; 514/44

(58) Field of Search .................. 435/177, 180, 435/181, 174, 178, 395; 424/484, 486, 489, 93.1, 93.7; 530/812, 813, 815; 514/44

(56) References Cited

U.S. PATENT DOCUMENTS

| | | | |
|---|---|---|---|
| 3,957,741 A | 5/1976 | Rembaum et al. | 526/312 |
| 3,985,632 A | 10/1976 | Rembaum et al. | 204/159.15 |
| 4,046,720 A | 9/1977 | Rembaum et al. | 260/2.5 B |
| 4,062,817 A | 12/1977 | Westerman | 260/17.45 G |
| 4,076,663 A | 2/1978 | Masudam et al. | 260/17.4 GC |
| 4,090,022 A * | 5/1978 | Tsao et al. | 536/57 |
| 4,177,056 A | 12/1979 | Mueller et al. | 71/93 |
| 4,188,373 A | 2/1980 | Krezanoski | 424/78 |
| 4,192,827 A | 3/1980 | Mueller et al. | 525/123 |
| 4,224,427 A | 9/1980 | Mueller et al. | 526/93 |
| 4,277,582 A | 7/1981 | Mueller et al. | 525/421 |
| 4,286,082 A | 8/1981 | Tsubakimoto et al. | 526/240 |
| 4,295,987 A | 10/1981 | Parks | 252/194 |
| 4,304,591 A | 12/1981 | Mueller et al. | 71/93 |
| 4,340,706 A | 7/1982 | Obayashi et al. | 526/207 |
| 4,379,138 A | 4/1983 | Pitt et al. | 424/78 |
| 4,452,973 A | 6/1984 | Casey et al. | 528/354 |
| 4,474,751 A | 10/1984 | Haslam et al. | 424/78 |
| 4,474,752 A | 10/1984 | Haslam et al. | 424/78 |
| 4,478,822 A | 10/1984 | Haslam et al. | 424/78 |
| 4,548,990 A | 10/1985 | Mueller et al. | 525/123 |
| 4,575,539 A | 3/1986 | DeCrosta et al. | 525/283 |
| 4,654,039 A | 3/1987 | Brandt et al. | 604/368 |
| 4,699,619 A | 10/1987 | Bernardin | 604/378 |
| 4,708,861 A | 11/1987 | Popescu et al. | 424/1.1 |
| 4,716,203 A | 12/1987 | Casey et al. | 525/408 |
| RE32,649 E | 4/1988 | Brandt et al. | 604/368 |
| 4,882,168 A | 11/1989 | Casey et al. | 424/468 |
| 4,938,763 A | 7/1990 | Dunn et al. | 604/891.1 |
| 4,942,035 A | 7/1990 | Churchill et al. | 424/423 |
| 4,950,264 A | 8/1990 | Osborn, III | 604/385.1 |
| 4,963,489 A | 10/1990 | Naughton et al. | 435/1.1 |
| 5,009,653 A | 4/1991 | Osborn, III | 604/385.1 |
| 5,057,560 A | 10/1991 | Mueller | 524/22 |
| 5,075,109 A | 12/1991 | Tice et al. | 424/88 |
| 5,077,210 A * | 12/1991 | Eigler et al. | 435/176 |
| 5,102,597 A | 4/1992 | Roe et al. | 264/126 |
| 5,147,923 A | 9/1992 | Mueller | 524/355 |
| 5,149,334 A | 9/1992 | Lahrman et al. | 604/367 |
| 5,180,622 A | 1/1993 | Berg et al. | 428/192 |
| 5,225,047 A * | 7/1993 | Graef et al. | 162/9 |
| 5,225,196 A | 7/1993 | Robinson | 424/427 |
| 5,252,318 A | 10/1993 | Joshi et al. | 424/78.04 |
| 5,330,822 A | 7/1994 | Berg et al. | 428/192 |
| 5,352,448 A | 10/1994 | Bowersock et al. | 424/438 |
| 5,397,626 A | 3/1995 | Berg et al. | 428/283 |
| 5,403,870 A | 4/1995 | Gross | 523/105 |
| 5,410,016 A | 4/1995 | Hubbell et al. | 528/354 |
| 5,415,864 A | 5/1995 | Kopecek et al. | 424/436 |

(List continued on next page.)

FOREIGN PATENT DOCUMENTS

| | | |
|---|---|---|
| DE | 201452 | 7/1983 |
| EP | 0368668 | 5/1990 |
| JP | 1199973 | 8/1989 |

OTHER PUBLICATIONS

Kurisawa et, al., Macromol. Chem. Phys. 199, 705–709 (1998).*

Domb et al., "Biodegradable Bone Cement Compositions Based on Acrylate and Epoxide Terminated Poly(Propylene Fumarate) Oligomers and Calcium Salt Compositions," *Biomaterials*, 17(4):411–417, 1996 Elsevevier Science Publishers.

(List continued on next page.)

*Primary Examiner*—David M. Naff
(74) *Attorney, Agent, or Firm*—Jackson Walker LLP

(57) ABSTRACT

Biodegradable cross-linkers are provided having a polyacid core with at least two acidic groups covalently connected to reactive groups usable to cross-link polymer filaments. Between at least one reactive group and an acidic group of the polyacid is a biodegradable region which preferably consists of a hydroxyalkyl acid ester sequence having 1, 2, 3, 4, 5 or 6 hydroxyalkyl acid ester groups. The polyacid may be attached to a water soluble region that is attached to the biodegradable region having attached reactive groups. The hydroxyalkyl acid ester group is preferably a lactate or glycolate. Polyacids include diacids, triacids, tetraacids and pentaacids, and the reactive group may contain a carbon-carbon double bond. A network of cross-linked polymer filaments having a defined biodegradation rate can be formed using the cross-linkers. The network may contain biologically active molecules, and can be in the form of a microparticle or nanoparticle, or hydrogel. The polymer filaments may be preformed polymer filaments of polynucleic acids, polypeptides, proteins or carbohydrates. The cross-linkers may be copolymerized with charged monomers such as acrylic monomers containing charged groups. Applications of the cross-linkers and network include controlled release of drugs and cosmetics, tissue engineering, wound healing, hazardous waste remediation, metal chelation, swellable devices for absorbing liquids and prevention of surgical adhesions.

30 Claims, 5 Drawing Sheets

U.S. PATENT DOCUMENTS

| | | | |
|---|---|---|---|
| 5,419,956 A | 5/1995 | Roe | 428/283 |
| 5,441,732 A | 8/1995 | Hoeg et al. | 424/78.04 |
| 5,462,866 A | 10/1995 | Wang | 435/174 |
| 5,474,768 A | 12/1995 | Robinson | 424/78.31 |
| 5,484,610 A | 1/1996 | Bae | 424/487 |
| 5,529,777 A | 6/1996 | Andrianov et al. | 424/184.1 |
| 5,549,791 A | 8/1996 | Herron et al. | 162/157.6 |
| 5,552,309 A | 9/1996 | March | 435/456 |
| 5,554,147 A | 9/1996 | Batich et al. | 604/890.1 |
| 5,567,435 A | 10/1996 | Hubbell et al. | 424/424 |
| 5,573,934 A | 11/1996 | Hubbell et al. | 435/177 |
| 5,593,974 A | 1/1997 | Rosenberg et al. | 514/44 |
| 5,601,542 A | 2/1997 | Melius et al. | 604/368 |
| 5,603,955 A | 2/1997 | Gehrke et al. | 424/484 |
| 5,607,417 A | 3/1997 | Batich et al. | 604/890.1 |
| 5,612,052 A | 3/1997 | Shalaby | 424/426 |
| 5,626,863 A | 5/1997 | Hubbell et al. | 424/426 |
| 5,627,233 A | 5/1997 | Hubbell et al. | 525/54.1 |
| 5,648,506 A | 7/1997 | Desai et al. | 549/510 |
| 5,652,225 A | 7/1997 | Isner | 514/44 |
| 5,656,481 A | 8/1997 | Baetge et al. | 435/325 |
| 5,665,428 A | 9/1997 | Cha et al. | 427/213.3 |
| 5,674,495 A | 10/1997 | Bowersock et al. | 424/184.1 |
| 5,674,521 A | 10/1997 | Gehrke et al. | 424/423 |
| 5,700,289 A | 12/1997 | Breitbart et al. | 623/16 |
| 5,702,717 A | 12/1997 | Cha et al. | 424/425 |
| 5,709,854 A | 1/1998 | Griffith-Cima et al. | 424/93.7 |
| 5,716,404 A | 2/1998 | Vacanti et al. | 623/8 |
| 5,744,166 A | 4/1998 | Illum | 424/501 |
| 5,750,585 A | 5/1998 | Park et al. | 521/143 |
| 5,783,567 A | 7/1998 | Hedley et al. | 514/44 |
| 5,788,687 A | 8/1998 | Batich et al. | 604/890.1 |
| 5,801,033 A | 9/1998 | Hubbell et al. | 435/182 |
| 5,834,274 A | 11/1998 | Hubbell et al. | 435/177 |
| 5,843,743 A | 12/1998 | Hubbell et al. | 435/177 |
| 5,858,746 A | 1/1999 | Hubbell et al. | 435/177 |
| 5,874,500 A | 2/1999 | Rhee et al. | 525/54.1 |
| 5,879,713 A | 3/1999 | Roth et al. | 424/489 |
| 5,885,829 A | 3/1999 | Mooney et al. | 435/325 |
| 5,900,238 A | 5/1999 | Gombotz et al. | 424/184.1 |
| 5,902,741 A | 5/1999 | Purchio et al. | 435/325 |
| 5,916,585 A | 6/1999 | Cook et al. | 424/426 |
| 5,919,753 A | 7/1999 | Klaveness et al. | 514/2 |
| 5,925,628 A | 7/1999 | Lee et al. | 514/169 |
| 5,932,241 A | 8/1999 | Gorman | 424/450 |
| 5,935,936 A | 8/1999 | Fasbender et al. | 514/44 |
| 5,939,323 A | 8/1999 | Valentini et al. | 435/395 |
| 5,942,209 A | 8/1999 | Leavitt et al. | 424/1.25 |
| 5,942,253 A | 8/1999 | Gombotz et al. | 424/501 |
| 5,944,754 A | 8/1999 | Vacanti | 623/11 |
| 5,945,100 A | 8/1999 | Fick | 424/93.21 |
| 5,981,739 A * | 11/1999 | Anderson et al. | 536/80 |

OTHER PUBLICATIONS

Elesseeff et al., "Cogelation of Hydrolyzable Cross–Liners and Poly(ethylene oxde) Dimethacrylate and Their Use as Controlled Release Vechicles", *ACM Symp. Ser.*, XP000925978, 728:1–13, Dec. 8, 1999.

Kiser et al., "Design and Performance of Poly(HPMA) Hydrogels Containing Symmetrical Biodegradable Crosslinkers Composed of Oligo–Lactate and Oligo–Glycolate Esters," *Polymer Preprints*, XP000925966, 41(1):712–713, Feb. 22, 2000.

Muggli et al., "Reaction Behavior of Biodegradable, Photo–Cross–Linkable polyanhydrides," *Macromolecules*, XP00765434 31(13):4120–4125, Jun. 30, 1998.

Storey et al., "New Epoxy–Terminated Oligoesters: Precursors to Totally Biodegradable Networks," *Journ. of Polymer Sci., Part A: Polymer Chemistry Edition*, XP000398513 31(7):1825–1838.

Abstract of JP 1199973, Aug. 11, 1989, XP002150448.

Antonietti, M.; Bremser, W.; and Schmidt, M. "Microgels: Model Polymers for the Cross–Linked State." *Macromolecules*, 23 (1990) 2796–3805.

Antonsen, K.; Robert J.; Nabeshima, Y,; Sheu, M.; Wu, X.; and Hoffman, A. "Controlled Release of Proteins from 2–Hydroxyethyl Methacrylate Copolymer Gels." *Biomat. Art. Cells & Immob. Biotech.*, 21 (1), 1–22 (1993).

Barbieri, R.; Quaglia, M.; Defini, J.; and Brosio, E. "Investigation of water dynamic behaviour in poly(HEMA) and poly (HEMA–co–DHPMA) hydrogels by proton $T_2$ relaxation time and self–diffusion coefficient n.m.r. measurements." *Polymer*, 39(5); (1998) 1059–1066.

Blau, H.; and Springer, M. "Gene Therapy—A Novel Form of Drug Delivery. [Molecular Medicine]" *New England Journal of Medicine*, vol. 333(18). Nov. 2, 1995, pp. 1204–1207.

Braet, F.; DeZanger, R.; Sasaoki, T.; Baekeland, M.; Janssens, P.; Smedsrø; and Wisse, E. "Methods in Laboratory Investigation, Assessment of a Method of Isolation, Purification, and Cultivation of Rat Liver Sinusoidal Endothelial Cells." *Laboratory Investigation*, 70(6); (1994) 944–952.

Brøndsted, H.; and Kopćcek, J. "Hydrogels for site–specific oral drug deliver: synthesis and characterization." *Biomaterials*, 12; (1991) 584–592.

Eichenbaum, G.; Kiser, P.; Simon, S.; and Needham, D. PH and Ion–Triggered Volume Response of Anionic Hydrogel Microspheres; *Macromolecules*, 31; (1993) 5084–5093.

Eichenbaum, G.; Kiser, P.; Shah, D.; Simon, S.; and Needham, D. "Investigation of the Swelling Response and Drug Loading of Ionic Microgels: The Dependence on Functional Group Composition." *Macromolecules* (submitted 1999).

English, A.; Mafé, S.; Manzanares, J.; Yu, X.; Grosberg, A.; and Tanaka, T. "Equilibrium swelling properties of polyampholytic hydrogels." *J. Chem. Phys.* 104 (21); (1996) 8713–8720.

Flory, P.; and Rehner, J., Jr. "Statistical Mechanics of Cross–Linked Polymer Networks." *The Journal of Chemical Physics*, 11(11); (1943) 521–526.

Franssen, O., Vandervennet, L.; Roders, P.; and Hennick, W.E. "Degradable dextran hydrogels: controlled release of a model protein from cylinders and microspheres." *Journal of Controlled Release*, 60 (1999).

Freed, K.; and Pesci, A. "Computation of the Cross–Link Dependence of the Effective Flory Interaction Parameter $\chi$ for Polymer Networks." *Macromolecules*, 22; (1989) 4048–4050.

Fukutomi, T.; Asakawa, K.; and Kihara, N. "Polyvinylalcohol Microgel." *Chemistry Letters*; (1997) 783–784.

Gaetjens, E.; and Morawetz, H. "Intramolecular Carboxylate Attack on Ester Groups. The Hydrolysis of Substituted Phenyl Acid Succinates and Phenyl Acid Glutarates." *J. Am. Chem. Soc.*, 82; (1960) 5328–5335.

Galli, A; and Brumage, W. "The freely jointed chain in expanded form." *J. Chem. Phys.*, 79(5); (1983) 2411–2418.

Graham, N.; and Cameron, A. "Nanagels and microgels: The new polymeric materials playground." *Pure & Appl. Chem.*, 70(6); (1998) 1271–1275.

Gregor, H. "Gibbs–Donnan Equilibria in Ion Exchange Resin Systems." *J. Am. Chem. Soc.*, 73; (1951) 642–650.

Grignon, J.; and Scallan, A.M. "Effect of pH and Neutral Salts upon the Swelling of Cellulose Gels." *Journal of Applied Polymer Science*, 25; (1980) 2829–2843.

Heller, J.; Helwing, R.F.; Baker, R.W.; and Tuttle, M.E. "Controlled release of water–soluble macromolecules from bioerodible hydrogels." *Biomaterials*, 4; (1983) 262–266.

Hu, Z.; Chen, Y.; Wang, C.; Zheng, Y. and Li, Y. Polymer gels with engineered environmentally reponsive surface patterns [Letters to Nature] *Nature*, vol. 393(6681)., May 14, 1998, pp. 149–152.

Isogal, N.; Landis, W.; Kim, T.; Gerstenfeld, L.; Upton, J.; and Vacanti, J. Formation of Phalanges and Small Joints by Tissue–Engineering [Articles] *The Journal of Bone and Joint Surgery (American Volume)*, 81–A(3), (1999) 306–316.

Jeong, B.; Bae, Y.; Lee, D.; and Kim, S. "Biodegradable block copolymers as injectable drug–delivery systems" *Nature*, 388(6645), (1007) 860–862.

Johnson, L. "Gene Therapy for Cystic Fibrosis [New Therapies for Cystic Fibrosis]" *Chest*, 107(2) Supplement (1995) 77S–83S.

Kashiwabara, M.; Fujimoto, K.; and Kawaguchi, H. "Preparation of Monodisperse, Reactive Hydrogel Micorspheres and their Amphotherization." *Colloid & Polymer Science*, 273; 339 (1995).

Kawaguchi, H.; Fujimoto, K.; Saito, M.; Kawasaki, T.; and Urakami, Y. "Preparation and Modification of Monodisperse Hydrogel Microspheres." *Polymer International*, 30(2); (1993) 225–231.

Kiser, P.; Wilson, G.; and Needham, D. "A synthetic mimic of the secretory granule for drug deliver." *Nature*, 394; (1998) 459–462.

Langer, R. "1994 Whitaker Lecture: Polymers for Drug Delivery and Tissue Engineering." *Annals of Biomedical Engineering*, 23; (1995) 101–111.

Marszalek, P.; Farrell, B.; Verdugo, P.; and Fernandez, J. "Kinetics of Release of Serotonin from Isolated Secretory Granules. 1. Amperometric Detection of Serotonin from Electroporated Granules." *Biophysical Journal*, 73; (1997) 1160–1168.

McKenna, G.; and Horkay, F. "Effect of crosslinks on the thermodynamics of poly (vinyl alcohol) hydrogels." *Polymer*, 35(26) (1994) 5737–5742.

Mikos, A.; and Peppas, N. "Flory interaction parameter $\chi$ for hydrophilic copolymers with water." *Biomaterials*, 9; (1988) 419–423.

Mulligan, R. "The Basic Science of Gene Therapy [Articles]" *Science*, 260(5110) (1993) 926–932.

Neyret, S.; and Vincent, B. "The properties of polyampholyte microgel particles prepared by microemulsion polymerization." *Polymer*, 38(25); (1997) 6129–6134.

Niklason, L.E.; Gao, J.; Abbott, W.M.; Hirschi, K.K.; Houser, S.; Marini, R.; and Langer, R. "Functional Arteries Grown in Vitro" *Science*, 284(5413) (1999) 489–493.

O'Mullane, J.; Artursson, P.; and Tomlinson, E. "Biopharmaceutics of Microparticulate Drug Carriers." *Annals New York Academy of Sciences*, 507; (1987) 120–140.

Ober, C.; and Lok, K. "Formation of Large Monodisperse Copolymer Particles by Dispersion Polymerization." *Macromolecules*, 20; (1987) 268–273.

Peppas, N.; and Langer, R. "New Challenges in Biomaterials [Materials Science: Articles.]" *Science*, 263(5154) (1994) 1715–1720.

Peppas, N.; Moynihan, H.; and Lucht, L. "The structure of highly crosslinked poly (2–hydroxyethyl methacrylate) hydrogels." *Journal of Biomedical Materials Research*, 19; (1985) 397–411.

Petka, W.; Harden, J.; McGrath, K.; Wirtz, D.; and Tirrell, D. "Reversible Hydrogels from Self–Assembling Artificial Protein [Research: Reports]" *Science*, 281(5375) (1998) 389–392.

Rembaum, A. "Synthesis, Properties and Biomedical Applications of Hydrophilic, Functional, Polymeric Immunomicrospheres." *Pure & Applied Chemistry*, 52; (1980) 1275–1278.

Rembaum, A.; Yen, S.P.S.; and Molday, R. "Synthesis and Reactions of Hydrophilic Functional Microspheres for Immunological Studies." *J. Macromol. Sci.–Chem.*, A13(5); (1979) 603–632.

Ricka, J.; and Tanaka, T. "Swelling of Ionic Gels: Quantitative Performance of the Donnan Theory." *Macromolecules*, 17; (1984) 2916–2921.

Rubinstein, M.; Colby, R.; Dobrynin, A.; and Joanny, J. "Elastic Modulus and Equilbrium Swelling of Polyelectrolyte Gels." *Macromolecules*, 29; (1996) 398–406.

Saunders, B.; Crowther, H.; and Vincent, B. "Poly[(methl methacrylate)–co–(methacrylic acid(] Microgel Particles: Swelling Control Using pH, Cononsolvency, and Osmotic Deswelling." *Macromolecules*, 30; (1997) 482–487.

Siegel, R. "Drug Delivery: A lesson from secretory granules [News and Views]" *Nature*, 392(6692) (1998) 427–428.

Tanaka, T.; and Fillmore, D. "Kinetics of swelling of gels." *J. Chem. Phys.*, 70(03); (1979) 1214–1218.

Tanaka, T.; Fillmore, D.; Sun, S.; Nishio, I.; Swislow, G.; and Shah, A. "Phase Transitions in Ionic Gels." *Physical Review Letters*, 45(20); (1980) 1636–1639.

Ulbrich, K.; Šubr, V.; Seymour, L.W.; and Duncan, R. "Novel biodegradable hydrogels prepared using the divinylic crosslinking agent N,O–dimethacryloylhydroxylamine. 1. Synthesis and characterisation of rates of gel degradation, and rate of release of model drugs, in vitro and in vivo." *Journal of Controlled Release*, 24; (1993) 181–190.

van Dijk–Wolthuis, W.N.W.; Hoogeboom, J.; van Steenbergen, M.; Tsang, S.; and Hennick, W. "Degradation and Release Behavior of Dextran–Based Hydrogels." *Macromolecules*, 30; (1997) 4639–4645.

van Dijk–Wolthuis, W.N.E.; Tsang, S.; Kettenes–van den Bosch, J.; and Hennick, W. "A new class of polymerizable dextrans with hydrolyzable groups: hydroxyethyl methacrylated dextran with and without oligolactate spacer." *Polymer*, 38(25); (1997) 6235–6242.

Wang, C.; Stewart, R.; and Kopecek, J. Hybrid hydrogels assembled from synthetic polymers and coiled–coil protein domains [Letters to Nature]⇆ *Nature*, 397(6718) (1999) 417–420.

Ando, S.; Putna, D.; Pack, D.W.; and Langer, R. "PLGA Microspheres containing plasmid DNA: Preservation of supercoiled DNA via cryopreparation and carbohydrate stabilization." *Journal of Pharmaceutical Sciences*, 88(1): 126–130 (1999) Abstract.

Burrish, H.; Vogel, C.; Schwarz, M.; Spencer, S.; Lentz, M., Abramson, N.; Eisenberg, P.; Fleming, F.; George, S.; and Sher, H. A phase I/II multicenter clinical trial of the cisplatin therapeutic implant (MPI 5010) for treatment of solid tumors (Meeting abstract). *Cancer Investigation*. 13 (Suppl 1):58–9, (1995). Abstract.

Coleman, E.A. "Commentary on gene therapy for cancer." [original article by Rosenberg, S. appears in JAMA, 268(17), 2416–2419 (1992)]. *ONS Nursing Scan in Oncology*, 2(2); 14 (1993). Abstract.

DiSilvio, L.; Guray, N.; Kayser, M.V.; Braden, M.; and Downes, S. "Biodegradable microspheres: a new delivery system for growth hormone." *Biomaterials*, 15(11); 931–936 (1994) Abstract.

Gombotz, W.R.; and pettit, D.K. "Biodegradable polymers for protein and peptide drug delivery." *Bioconjugate Chemistry*, 6(4); 332–351 (1995) Abstract.

Johnson, L.G. "Gene therapy for cystic fibrosis." *Chest: The Cardiopulmonary Journal*, 107(Supp.2); 775–835 (1995) Abstract.

Kaleta–Michaels, S.; Yu, N.; Singh, S.; Luck, E.; and Brown, D. Drug retention in prostate and liver after intraorgan injection of sustained–release 5–fluorouracil and methotrexate therapeutic implants (Meeting abstract). Proc. Annu. Meet. Am. Assoc. Cancer Res. 34;A2186. (1993). Abstract.

Kanekal, S.; Sahai, A.; Jones, R.; and Brown, D. "Enhanced retentio of 195 Pt–cisplatin in murine tumors with a novel injectable sustained–release drug delivery system." (Meeting abstract). Proc. Annu. Meet. Am. Assoc. Cancer Res. 36:A1844. (1995). Abstract.

Krol, A. Commentary on Gene therapy of cancer [original article by Freeman, S. et al appears in Cancer Invest., 11(6), 676–688 (1993)]. *ONS Nursing Scan in Oncology*, 3(3); 16 (1994) Abstract.

Langer, R. "1994 Whitaker Lecture: polymers for drug delivery and tissue engineering." *Annals of Biomedical Engineering*, 23(2); 101–111 (1995) Abstract.

Ning, S.; Trisler, K.; Brown, D.; Yu, N.; Kanekal, S.; Lundstan, M.; and Knox, S. "Intratumoral radioimmunotherapy of a human colon cancer xenograft using a sustained–release gel." *Radiotherapy & Oncology*, 39(2); 179–1890 (1996) Abstract.

Ning, S.; yu, N.; Brown, D.; Kaneka, S.; and Knox, S. "Radiosensitization by intratumoral administration of cisplatin in a sustained–release drug delivery system." *Radiotherapy & Oncology*, 50(2); 215–223 (1999). Abstract.

Pistel, K.; Bittner, B.; Koll, H.; Winter, G.; and Kissel, T. "Biodegradable recombinant human erythropoietin loaded microspheres prepared from linear and star–branched block copolymers: influence of encapsulation technique and polymer composition on particle characteristics." *Journal of Controlled Release*, 59 (3); 309–325 (1999). Abstract.

Richardson, S.C.W.; Kolbe, H.J.V.; and Duncan, R. "Potential of low molecular mass chitosan as a DNA delivery system: biocompatibility, body distribution and ability to complex and protect DNA." *International Journal of Pharmaceutics*, 178(2); 231–243 (1999). Abstract.

Ruponen, M; Yla–Herttuala, S.; and Urtti, A. "Interactions of polymeric and liposomal gene delivery systems with extracellular glycosaminoglycans: physicochemical and transfection studies." *Biochemica et Biophysica Acta–Biomembranes*, 1415(2); 331–341 (1999) Abstract.

Sahai, A.; Kanekal, S.; Jones, R.; and Brown, D. An injectable sustained–release drug delivery system markedly enhances intratumoral retentio of 14C–fluorouracil in murine fibrosarcomas (Meeting abstract). Proc. Annu. Meet. Am. Assoc. Cancer Res.; 36:A1843 (1995) Abstract.

Smith, J.P.; Liu, G.; Stock, E.; Orenberg, E.K.; Uy, N.Y.; and Brown, D.M. "Intratumoral chemotherapy in therapeutic implants inhibits growth of human pancreatic cancer xenografts." (Meeting abstract) Proc. Annu. Meet. Am. Assoc. Cancer Res. 36:A1843. (1995). Abstract.

Smith, J.; Liu, G.; Stock, E.; Orenberg, E.; Yu, N.; and Brown, D. "Intratumoral chemotherapy with a sustained–release drug delivery system inhibits growth of human pancreatic cancer xenografts." *Anti–Cancer Drugs*, 6(6); 717–726 (1995) Abstract.

Weber, C. "Cytokine–modified tumor vaccines: an antitumor strategy revisited in the age of molecular medicine." *Cancer Nursing*, 21(3); 167–177 (1998). Abstract.

Author Anonymous. Enhanced retention of CH–camptothecin in murine RIF–1 tumors with an injectable sustained–retention drug delivery system (Meeting abstract). Proc. Annu. Meet. Am. Assoc. Cancer Res. 38:A1743. (1997). Abstract.

Ando, S.; Putnam, D.; and Langer, R. In Vitro Evaluation of Biodegradable Microspheres as a Vector for Gene Delivery Systems; Proceed. Int'l. Symp. Contro. Rel. Bioact. Mater., 26 (1999) Controlled Release Society, Inc., #5902.

Cho, J.; Kim, O.; and Choi, H. "Methoxy Poly Ethylene Glycol/Poly (Acrylic Acid) Interpolymer Complex for Transmucosal Drug Delivery." Proceed. Int'l. Symp. Control. Rel. Bioact. Mater., 26 (1999) Controlled Release Society, Inc., #5025.

Daugherty, A.; Steinmetz, H.; Hoeffel, J.; Duenas, E.; Tobin, P.; Peale, F.; Ryan, A.; Bunting, A; and Cleland, J. "VEGF Loaded Microspheres Injected Intramuscularly produce local neovascularization in normal, aged C57BL–6 Mice." Proceed. Int'l. Symp. Control. Rel. Bioact. Mater., 26 (1999) Controlled Release Society, Inc., #6804.

Foss, A.; McClay, R.; and Peppas, N. "P(AA–g–PEG) Copolymer gels as carries for delivery of chemotherapeutic agents." Proceed. Int'l. Symp. Control. Rel. Bioact. Mater., 26 (1999) Controlled Release Society, Inc., #6341.

Gemeinhart, R.; Park, H.; and Park, K. "Structures of Superporous Hydrogels in the Dried and Swollen States." Proceed. Int'l. Symp. Control. Rel. Bioact. Mater., 26 (1999) Controlled Release Society, Inc., #5549.

Haensler, J. "DNA Vaccines: Mechanisms of Immune Stimulation." Proceed. Int'l. Symp. Control. Rel. Bioact. Mater., 26 (1999) Controlled Release Society, Inc., #116.

Khan, A.; Harris, S.; Beck, G.; and Akhtar, S., "In–Vivo Sustained Delivery of Antisense Oligonucleotides: Biodistribution studies and Release Profiles in Mice using Whole Body Autoradiography." Proceed. Int'l. Symp. Control. Rel. Bioact. Mater., 26 (1999) Controlled Release Society, Inc., #345.

Kostarelos, K.; Edwards, K.; Almgren, M.; Luckham, P.F.; and Tadros, Th.F. "Engineering Novel Vesicles Towards Gene Therapy Applications: The Fusogenic Sterically Stabilized Liposomes." Proceed. Int'l. Symp. Control. Rel. Bioact. Mater., 26 (1999) Controlled Release Society, Inc., #6454.

Luo, D.; Woodrow–Mumbord, K.; Belcheva, W.; and Saltzman, M. "Controlled Release of DNA from EVAC, PLGA, and PLA." Proceed. Int'l. Symp. Control. Rel. Bioact. Mater., 26 (1999) Controlled Release Society, Inc., #6438.

Nwachuku, J.N.; Ashford, M.; and Pouton, C.W. "Gene Transfer Using a Bifunctional Peptide." Proceed. Int'l. Symp. Control. Rel. Bioact. Mater., 26 (1999) Controlled Release Society, Inc., #5220.

Pardoll, D.M. "Geographically Localized Cytokine Released as a Fundamental Concept in Immunotherapy." Proceed. INt'l. Symp. Control. Rel. Bioact. Mater, 26 (1999) Controlled Release Society, Inc., #213.

Saltzman, W.M. "Disease Prevention using Orally Active Vaccines." Proceed. Int'l. Symp. Control. Rel. Bioact. Mater., 26 (1999) Controlled Release Society, Inc., #246.

Smith, D.; Volsen, S.; Moore, N.; Craig, P.; and Akhtar, S. "The Sustained Delivery of Antisense Oligodeoxynucleotides into the CNS Using Biodegradable Microspheres: In Vitro and In Vivo Studies." Proceed. Int'l. Symp. Control. Rel. Bioact. Mater., 26 (1999) Controlled Release Society, Inc., #6339.

Song, S.-C.; Lee, S.B.; Jin, J.-I; and Sohn, Y.S. "A New Class of Biodegradable Thermosensitive Polymers: II. Hydrolytic Properties of Poly(Organophosphazenes) With Methoxy–Poly(Ethylene Glycol) and Amino Acid Esters." Proceed. Int'l. Symp. Control. Rel. Bioact. Mater., 26 (1999) Controlled Release Society, Inc., #5930.

Tinsley–Brown, A.M.; Mobsby, V.A.; Outlaw, M.C.; and Farrar, G.H. "DNA Release From PLGA Microparticles for Vaccine Applications." Proceed. Int'l. Symp. Control. Rel. Bioact. Mater., 26 (1999) Controlled Release Society, Inc., #344.

Wolff, J.A. "Mechanism of Gene Transfer by Naked DNA." Proceed. Int'l. Symp. Control. Rel. Bioact. Mater., 26 (1999) Controlled Release Society, Inc., #117.

Yu, C.; Simons, M.; and Edelman, E. "Controlled Release of Endothelial Growth Factors for Local Intervention of Vascular Diseases and Angiogenesis." Proceed. Int'l. Symp. Control. Rel. Bioact. Mater., 26 (1999) Controlled Release Society, Inc., #126.

Cohen, H.; Golomb, G.; and Levy, R. "Gene Delivery by Polymer–Encapsulated DNA." Source Unknown; Author's location: School of Pharmacy, The Hebrew University of Jerusalem, Jerusalem, Israel.

Liu, L–S.; Ng. C.K.; Thompson, A.; Radomsky, M.L.; Poser, J.W.; and Spiro, R.C. "The Bioactivity and Stability of bFGF in a Novel Hyaluronate/Heparin Conjugate." Source Unknown. Author's location: Orquest. Inc., 365 Ravendale Drive, Mountain View, CA 94043 USA.

Mao, H.–Q.; Lin, K.Y.; Liu, S.–Q., Haller, M.F.; and Leong, K.W. Intramuscular Delivery of Plasmid encapsulated in Biodegradable Poly(D,L–Lactide–co–Phosphate) Microspheres. Source Unknown. Author's Location: Dept of Biomedical Engineering, The Jons Hopkins School of Medicine, Baltimore, MD 21205.

Walter, E.; Moelling, K.; Pavlovic, J.; and Merkle, H. Poly(DL–Lactide–CO–Glycolide)–Encapsulated DNA: Stability and Release Characteristics. Source Unknown. Author's Location: Department of Pharmacy, ETH Zurich, Winterthurerstrasse 190, CH–8057 Zurich.

Wasan, E. "Targeted Gene Transfer." Source Unknown. Author's Location: Department of Advanced Therapeutics, BC Cancer Agency, Department of Pathology and Laboratory Medicine, University of British Columbia.

* cited by examiner

STRUCTURE A

STRUCTURE B

STRUCTURE C

STRUCTURE D

US 6,521,431 B1

BIODEGRADABLE CROSS-LINKERS HAVING A POLYACID CONNECTED TO REACTIVE GROUPS FOR CROSS-LINKING POLYMER FILAMENTS

BACKGROUND OF THE INVENTION

The present invention relates to novel cross-linking agents, more particularly to novel biodegradable cross-linking agents. Earlier use of cross-linking agents in a variety of fields involving proteins, carbohydrates or polymers is well established. Even biodegradable cross-links have previously been prepared and utilized. However, none before have utilized particular and advantageous cross-linker designs of the present invention.

Within the pharmaceutical, agricultural, veterinary, and environmental industries, much attention has been directed to the applications of biodegradable polymers. The Oxford English dictionary defines biodegradable as: "susceptible to the decomposing action of living organisms especially bacteria or broken down by biochemical processes in the body." However, due to the advent of the widespread use of polyhydroxyacids as degradable polymers, this definition should be extended to include non-enzymatic chemical degradation which can progress at an appreciable rate under biologically relevant conditions (the most relevant condition being water at pH 7; 100 mM salt and 37° C.). Thus, the meaning of the term biodegradation can be broadened to include the breakdown of high molecular weight structures into less complicated, smaller, and soluble molecules by hydrolysis or other biologically derived processes.

In the biomaterials/pharmaceutical area, there is great interest in the use of biodegradable materials in vivo, due to performance and regulatory requirements. However, most of the reports on biodegradable materials have focused on linear water-insoluble hydroxyacid polyesters. Much less work has been done on biodegradable network polymers which are cross-linked. Therefore, due to the unique properties of network polymers, it is to be expected that biodegradable networks will find many new and important applications

Biodegradable Polymers

Much work has been accomplished in the last 20 years in the area of hydrophobic biodegradable polymers, wherein the biodegradable moieties comprise esters, lactones, orthoesters, carbonates, phosphazines, and anhydrides. Generally the polymers made of these biodegradable linkages are not water soluble and therefore in themselves are not amenable for use in systems where water is required, such as in hydrogels.

Since the mechanism of biodegradation in these polymers is generally through the hydrolytically-active components of water (hydronium and hydroxide ions), the rate of hydrolytic scission of the bonds holding a polymer network together is generally pH sensitive, with these moieties being susceptible to both specific-acid catalyzed hydrolysis and base hydrolysis. Other factors affecting the degradation of materials made of these polymers are the degree of polymer crystallinity, the polymer volume fraction, the polymer molecular weight, the cross-link density, and the steric and electronic effects at the site of degradation.

Degradable Network Structures

Biodegradable network structures are prepared by placing covalent or non-covalent bonds within the network structure that are broken under biologically relevant conditions. This involves the use of two separate structural motifs. The degradable structure is either placed into (i) the polymer backbone or (ii) into the cross-linker structure. The method described herein creates a degradable structure through placing degradable regions in the cross-linking domain of the network. One of the first occurrences of degradable hydrogels was published in 1983 by Heller. This system contains a water soluble linear copolymer containing PEG, glycolylglycolic acid and fumaric acid linkages. The fumaric acid allowed the linear polymer to be cross-linked through free radical polymerization in a second network forming polymerization step, thus creating a polymer network which could degrade through hydrolysis of the glycolic ester linkages. This is an example of creating degradable linkages in the polymer backbone.

Biodegradable Cross-linkers

The first truly degradable cross-linking agents were made from aryl diazo compounds for delivery of drugs in the digestive tract. The diazo moiety is cleaved by a bacterial azoreductase which is present in the colon. This has been used to create colon specific delivery systems (Brondsted et al. & Saffan et al.). Another biodegradable cross-linking agent appears in the work of Ulbrich and Duncan where a bis-vinylic compound based on hydroxyl amine was synthesized. Hydrogels made from this degradable cross-linker were shown to undergo hydroxide induced hydrolysis of the nitrogen-oxygen bond.

Hubbell et al. have made hydrogels composed of macromonomers composed of a central PEG diol which was used as a bifunctional alcohol in the tin octanoate catalyzed transesterifying ring opening polymerization of lactide to give a bis-oligolactate PEG. This compound was then reacted with acryloyl chloride to give a macromolecular cross-linker which could be formed into a homo-polymer interpenetrating network of PEG and oligolactylacrylate through free radical polymerization (Pathak et al.). Hubbell mostly intended these compounds for use as photopolymerizable homo-polymers useful to prevent surgical adhesions.

A second solution to this problem has been recently reported in the work of Van Dijk et al. which is the first report of a biodegradable cross-linking macromonomer composed of alpha-hydroxy esters (Van Dijk-Wolthius et al.). This work combines natural polymers with synthetic polymers in an interpenetrating network. This group functionalized dextran with oligo-alpha hydroxy acid domains which were end capped with vinyl regions that were polymerized into biodegradable networks via free radical polymerization.

The most recent report of a biodegradable cross-linking agent was one designed to undergo enzymatic degradation. This cross-linker is composed of a centro-symmetric peptide terminated by acrylamide moieties with a central diamine linking the two ends (Kurisawa et al.). This report is related to the invention described herein in that the property of biodegradability is built into the polymer network by first synthesizing a small symmetrical cross-linker which can undergo cleavage, then incorporating this in a polymer network.

Properties of Degradable Gels: Swelling and Porosity

Since degradability is a kinetic effect, the properties of degradable gel networks are the similar to those standard gel networks, except they change with time. The two main properties that are exhibited by degradable hydrogel networks are swelling and network porosity that increase with time as the network degrades.

The main feature observed with degradable cross-linked polymer networks in solvents which cause them to swell is that the polymer network swells as it degrades. This is because network degradation results in a decrease in cross-link density. As the cross-link density decreases there is more available volume for solvent within the network. The solvent increasingly permeates the network structure, driven by a favorable thermodynamic mixing of solvent with the polymer network.

Important uses envisioned for degradable gels are as controlled drug delivery devices and as degradable polymers for other in vivo uses. These devices are able to change from a high viscosity material (gel) to a lower viscosity soluble material (sol). The resulting water soluble linear polymer can then be readily transported and excreted or degraded further.

Degradable hydrogel networks offer the opportunities to effect the diffusitivity of materials bound in the hydrogel network, because as the network degrades the diffusion coefficient of molecules in the network increases with time thus facilitating the release of materials locked within the polymer network (Park).

Moreover, because the hydrogel network structure itself is of such a high molecular weight, transport of the hydrogel network out of the body or environment is slow. This is especially true in vivo where non-degradable implanted hydrogel networks can remain in the body for many years (Torchilin et al.). Therefore, such devices would be more useful if they could be made of a high molecular weight polymer that would degrade into smaller molecular weight components after the device has performed its task and then could be excreted through normal routes of clearance.

Since excretion of polymers is molecular weight-dependent (Drobnik et al.), with the preferred route being through the renal endothelia (Taylor et al. & Tomlinson), the chains making up the polymer backbone should be between 10 and 100 kDa. Because the material is engineered to degrade into excretable parts, biodegradable hydrogel networks offer increased biocompatibility.

Biodegradable Network Polymers as Controlled Release Depots

Biodegradable network polymers can be used as carriers for biologically active substances. These include proteins, peptides, hormones, anti-cancer agents antibiotics, herbicides, insecticides and cell suspensions. The hydrophilic or hydrophobic polymer network can act as a stabilizing agent for the encapsulated species and as a means to effect a controlled release of the agent in to the surrounding tissue or systemic circulation. By changing the size of the depot, the degree of porosity, and the rate of degradation (through modification of the degradable regions in the polymer network) controlled release depots with a variety of release characteristics can be fashioned for application in the medical and diagnostic areas.

Biodegradable Network Polymers as Water Adsorbents

Owing to the ability of hydrophilic network polymers to adsorb water, biodegradable versions of these networks may prove to have many uses in items for example, sanitary napkins, wound dressings, and diapers. When these materials are used in consort with other degradable materials a completely biodegradable and disposable product could be produced. Although a literature search in the Chemical Abstracts database for biodegradable adsorbents produced no citations, the use of degradable adsorbents in the above mentioned products would be very desirable.

Biodegradable Network Polymers as Adhesives

There is a great need for biodegradable adhesives and sealers in surgery and elsewhere. Synthetic polymers have been used as adhesives in surgery with the cyano acrylate esters being the most commonly cited. Recent reports using biodegradable networks as sealants in dentistry and orthopedics have displayed the utility of biodegradable polymers (Burkoth). Here the use of a biodegradable cross-linking monomer (bis-methacrylated diacid anhydride) which has been photopolymerized is envisioned for use in dentistry. Here a hydrophobic network-forming monomer is photopolymerized in situ to form a mechanically stable and non-swellable bonding material. Degradability would be a desirable property for any short term application and of course would be undesirable for long term applications.

Use of Biodegradable Polymers in Drug Delivery

Since most biodegradable polymers are not soluble in water, a hydrophilic drug is formulated in these polymers by a dispersion method using a two phase system of water (containing drug) and organic solvent (containing the polymer). The solvent is removed by evaporation resulting in a solid polymer containing aqueous droplets. This type of system suffers from the need to use organic solvents which would be undesirable for protein delivery since the solvent may denature the protein. Therefore it is envisioned that hydrophilic biodegradable network polymers will improve the range of drugs delivered from this general glass of polymers.

Biodegradable Nanoparticles

The use of nanoparticles for colloidal drug delivery has been a goal of formulation scientists for the last 20 years. Nanoparticles are defined as any solid particle between 10 and 1000 nm and are composed of natural or more commonly synthetic polymers. The most useful method of production for the lower end of this size range is emulsion polymerization, where micelles act as a reaction template for the formation of a growing polymer particle. For passive delivery of anticancer agents to tumors, nanometer size particles (50–200 nm) are required. The small size is required for extravasation of the nanoparticles through the permeable tumor vasculature in a process termed the EPR effect (enhanced permeability and retention) (Duncan).

Another important feature of any nanocarrier is the biocompatibility of the particle. This requires that the polymer particle degrades after some period so that it may be excreted. These criteria require polymer compositions that are well tolerated. To date there are no reports in the literature of degradable nanogels composed of well-tolerated parenteral polymers.

Hydrogel particles can be made in several sizes according to the performance requirements of the drug delivery system being engineered. Gel particles in the nanometer size range that are capable of being retained in tumor tissue are preferred for delivery of anticancer agents. Methods for the creation of approximately 100 nm in diameter hydrogel particles involve the use of surfactant-based emulsion polymerizations in water. To make ionomeric nanogels by this method it is necessary to include a hydrophobic component in the monomer mixture, thus allowing partitioning of the monomers into the micellar phase followed by particle nucleation and further monomer adsorption (normally emulsion polymerizations are used to make hydrophobic latexes).

Another important consideration is the means by which the carrier will load the drug substance to be delivered. The loading capacity of non-ionic hydrogels is generally limited by the aqueous solubility of the drug. However if the drug is charged, groups of opposite charge to the drug can be incorporated into the polymer to allow high drug loading through ion exchange. An interesting and perhaps useful property resulting from inclusion of charged monomers in the polymer network is a pH induced volume response of the polymer.

Current State of the Art

To date most biodegradable polymers have been synthesized using stepwise condensation of monomer resulting in a polydispersed molecular architecture. Since the rate of degradation is in part directly related to this architecture, this method results in the undesirable property that the material will contain cross-links with a variety of degradation rates. Secondly, since synthetic biodegradable polymers are generally water insoluble, there is a need for degradable moieties that are readily incorporated into water soluble monomers or polymers. Biodegradable moieties based on the non-soluble degradable units can be combined with water soluble oligomeric regions or polymers, resulting in a biodegradable structure.

Therefore as an object of the present invention the new material would have the preferred characteristics that it was easily synthesized, composed of biocompatible components, and have a well defined molecular structure leading to defined biodegradation rates.

It is a further object of the present invention that it be easily incorporated in many different polymer processing options such as polymer microparticles, nanoparticles and slab gels.

Therefore, the use of organic synthesis methodology to incorporate monodispersed degradable sequences into the monomer structure before polymer formation permits control of overall degradation as well as the release rate of entrapped substances.

Previous work in the area of creating biodegradable cross-linkers by Hubbel teaches a method to create degradable sequences using ring opening polymerization of lactide or glycolide. This method creates a mixture of degradable units with varying molecular weights or chain lengths in the end product. The present invention described herein teaches a method of stepwise synthesis of the degradable region which creates a pure compound at the end of the synthesis. Therefore, since the length of the degradable region will be the major structural determinant of the degradation rate, the present invention provides for a more controlled degradation rate than the Hubbel invention. Our invention also provides compounds which will be easier to purify than the Hubbel invention owing to stepwise syntheses of the degradable region and the resulting purity of the reaction product. Other advantages of our invention over Hubbel's invention are that the invention described herein is applicable to hydrophobic networks as well as hydrophilic networks whereas Hubbel is restricted to hydrophilic networks, and the invention herein can generate all useful properties such as rapid degradation rate and water solubility through the syntheses of oligomeric cross-linking compounds without resorting to polymeric cross-linking compounds.

The present preferred embodiment of this invention is as cross-linkers which are composed of a symmetrical diacid attached to at least one biodegradable region. These regions may consist of alpha hydroxy acids such as glycolic or lactic acid. These degradable portions are then terminated directly or indirectly by a functional group which may be polymerized. Moreover component pieces of the degradable gel such as lactic, glycolic and succinic acids are members of the Krebs cycle and therefore readily metabolized in vivo, while the end groups become incorporated into water-soluble polymer, which is eliminated by renal excretion.

SUMMARY OF THE INVENTION

In one important aspect the present invention concerns a monomeric or oligomeric cross-linker comprising a polyacid core with at least two acidic groups directly or indirectly connected to a reactive group usuable to cross-link polymer filaments, with at least one acidic group being connected to a region degradable under aqueous conditions and the degradable regions or (in the case of a single degradable region), the degradable region at at least one other acidic group directly or indirectly having a covalently attached reactive group usable to cross-link polymer filaments interceding between the acidic group and a reactive group. Thus the at least two reactive groups are always interspaced by at least one degradable region. In many preferred applications, the cross-linker is utilized to cross-link water soluble polymeric filaments. The polyacid core may be attached to a water soluble region that is in turn attached to a degradable region (or vice versa) having an attached reactive group. A polycarboxylic acid is the preferred polyacid. The polyacid core is preferably a diacid, triacid, tetraacid or pentaacid. The most preferred polyacid core is a diacid. Preferred polyacids or polycarboxylic acids. Alkyl-based diacids such as malonic, succinic, adipic, fumaric, maleic, sebacic and tartaric are preferred. Diacids such as succinic, adipic or malonic acid are particularly preferred. A triacid such as citric acid, for example, is usable. Tetra-and penta-acids such as ethylenediamine tetraacidic acid (EDTA) or diethylenetramine pentaacetic acid (DTPA) are usable, for example. When cross-linked polymer filaments are formed according to the present invention, they are cross-linked by a component having at least one degradable region. Preferred degradable regions include poly (alpha-hydroxy acids), although other hydroxy alkyl acids that may form polyesters can be used to form biodegradable regions. Preferred polyesters include those of glycolic acid, DL lactic acid, L lactic acid, oligomers, monomers or combinations thereof. Cross-linkers of the present invention may also include a degradable region containing one or more groups such as anhydride, a orthoester and/or a phosphoester. In certain cases the biodegradable region may contain at least one amide functionality. The cross-linker of the present cross-linker may also include an ethylene glycol oligomer, oligo(ethylene glycol), poly(ethylene oxide), poly (vinyl pyrolidone), poly(propylene oxide), poly (ethyloxazoline), or combinations of these substances.

Preferred reactive groups are those that contain a carbon-carbon double bond, a carbonate, a carbamate, a hydrazone, a hydrazino, a cyclic ether, acid halide, a acylazide, succinimidyl ester, imidazolide or amino functionality. Other reactive groups may be used that are known to those skilled in the art to be precursors to polymers.

Utilizing the cross-linkers of the present invention, networks of polymer filaments may be formed by thermal, catalytic or photochemical initiation. Networks of polymer filaments may likewise be formed by pH changes. Networks of polymer filaments may also be formed for example by free radical addition or Michael addition.

The present invention comprises a network of polymer filaments formed by precipitation or emulsion polymerization and cross-linked by a monomeric or oligomeric cross-linker comprising a poly acid core with at least one acidic group connected to a region degradable under in vivo conditions and having at least two covalently attached reactive groups usable to cross-link polymer filaments. Polymeric filaments to be cross-linked include preformed polymer filaments such as polynucleic acids, polypeptides, proteins or carbohydrates. Such cross-linked polymeric filaments may be utilized to contain biologically active molecules. The biologically active molecules may be organic molecules, proteins, carbohydrates, polynucleic acids, whole cells, tissues or tissue aggregates.

The preferred monomeric or oligomeric cross-linker of the present invention has a polyacid core with a molecular weight between about 60 and about 400 Daltons. The degradable region(s) has a preferable molecular weight range of about 70 to about 500 Daltons. The reactive groups of the cross-linker of the present invention may be end groups and have preferred molecular weights between about 10 and 300 Daltons.

An important aspect of the present invention is a monomeric or oligomeric cross-linker comprising a polyacid core with at least two esterified groups being connected (directly or indirectly) to reactive groups usable to cross-link polymer filaments. Between at least one reactive group and polyacid core is a region degradable under aqueous conditions. Thus the cross-linker is usable to form cross-linked polymer filaments. In a preferred embodiment, the polyacid core has two acidic groups connected to a region degradable under aqueous conditions, each having a covalently attached reactive group usable to form cross-linked polymer filaments. In certain cases the cross-linkers of the present invention may contain a water soluble region located between at least one carboxyl group and its associated reactive group. A preferred polymer filament for cross-linking is a hydrogel. In certain cases the polymer filament being cross-linked may be hydrophobic.

In many cases the polyacid core of the present inventive cross-linker is a diacid, such as for example succinic acid, adipic acid, fumaric acid, maleic acid, sebacic acid or malonic acid. Triacids such as citric acid are also usable. Other triacids will be apparent to those of skill in the art. Tetraacids and pentaacids may also be used. A preferred tetraacid is ethylene diamine tetraacetic acid (EDTA) and a preferred pentaacid is diethylenetriamine pentaaceticic acid (DTPA).

Acids that may be used as a polyacid core include citric acid, tartaric acid and the like. A preferred biodegradable region for use in the cross-linkers of the present invention is one that comprises a hydroxy alkyl acid ester. A preferred hydroxy acid ester is an alpha hydroxy acid ester. Under some circumstances the degradable region may be a peptide. Preferred degradable polyesters include glycolic polyester, DL lactic acid polyester and L lactic acid ester or combinations thereof. In certain cases the degradable region of the cross-linker of the present invention may comprise an anhydride, orthoester or phosphoester linkages. In certain cases the reactive group of the present inventive cross-linker contains a carbon-carbon double bond. In some cases the reactive group is an end group, e.g. at the end of a degradable region. The reactive group may also contain a carbonate, carbamate hydrazone, hydrazino, cyclic ether, acid halide, acyl azide, succinimidyl ester, imidazolide or amino functionality.

The cross-linker of the present invention may be utilized to form networks of polymer films formed by thermal catalytic or photochemical initiation. In certain cases networks of polymer films may be formed as induced by a pH change and then cross-linked. In other cases, networks of polymer films may be formed through reactions involving free radical addition or Michael addition. The aqueous conditions under which the cross-linkers of the present invention are degradable are most frequently physiological conditions.

In an important aspect, the present invention comprises a network of polymer filaments formed by precipitation, dispersion or emulsion polymerization and cross-linked by a monomeric or oligomeric cross-linker having a polyacid core with at least two esterified groups connected to a covalently attached reactive group used to cross-link polymer filaments and at least one acidic group having a region degradable under aqueous conditions between the acidic group and the reactive group.

Also included in the present invention are networks of polymer filaments of polynucleic acids, polypeptides, proteins or carbohydrates and cross-linked by a monomeric or oligomeric cross-linker comprising a polyacid core with at least two esterified groups connected to at least one region degradable under in vivo conditions, and having a covalently attached reactive group cross-linking the polymer filaments.

In both cases of networked polymer filaments, these networks may contain biologically active molecules. Because the cross-links are degradable, these biological molecules will be expected to be released.

In one important aspect, the present invention comprises a network of polymer filaments cross-linked by a monomeric or oligomeric cross-linker comprising a polyacid core with at least two acidic groups connected to at least one region degradable under in vivo conditions, and both acidic groups connected to a covalently attached reactive group and defined further as comprising an organic molecule, inorganic molecule, protein, carbohydrate, poly(nucleic acid), cell, tissue or tissue aggregate.

Additionally, the invention includes a network of polymer filaments cross-linked by monomeric or oligomeric cross-linker comprising a central polyacid core with at least two acidic groups connected to at least one region degradable under in vivo conditions, and terminated by a covalently attached reactive end group usable to cross-link polymer filaments, the network comprising an organic radioisotope, inorganic radioisotope or nuclear magnetic resonance relaxation reagent.

According to the present invention the polyacid core has a preferred molecular weight between about 60 and about 400 daltons. The degradable region of the cross-linker has a preferred molecular weight between about 70 and about 500 daltons. The reactive groups of the present invention generally have molecular weights between about 10 and about 300 daltons.

DESCRIPTION OF PREFERRED EMBODIMENTS

Figure 1:
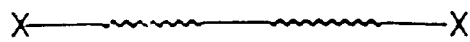
FIG. 1 schematically illustrates a representative lactate-based cross-linking agent of the present invention.
Figure 1:
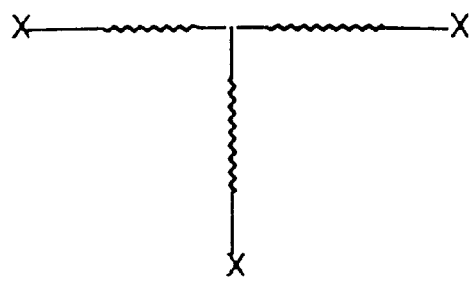
Figure 1:
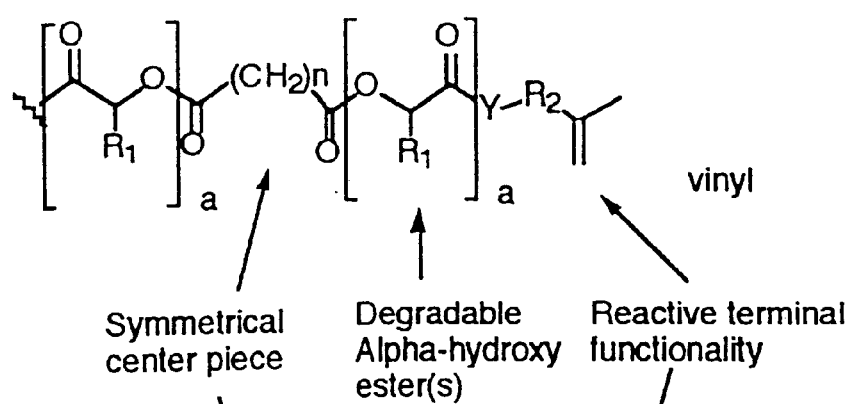
Figure 1:
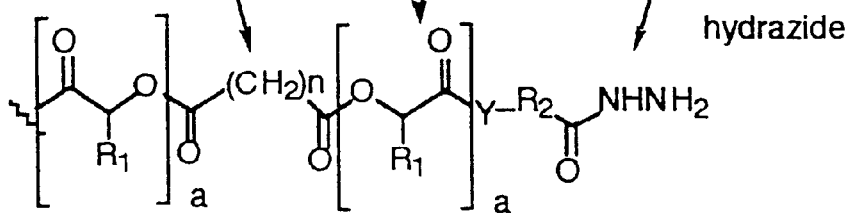

This invention discloses a representative synthesis and application of symmetrical biodegradable cross-linking agents for use in cross-linked polymer matrices formed into particles or slabs that may be used e.g., in drug delivery. The cross-linking agents will be monomers or oligomers of biocompatible units in the preferred biological applications. In the preferred practice of this invention the cross-linker is composed of a central diacid (such as succinic); to this diacid is attached one or more biodegradable regions, which are then terminated by reactive moieties which are used for incorporation into the polymer network. This invention requires there be at least two reactive moieties (two representative cross-linkers are depicted in FIG. 1). The cross-linkers may be incorporated into matrices of various sizes ranging from hundreds of cm's to 10 nm so as to control the diffusion of substance such as drugs e.g., from the matrix by biodegradation of the cross-linkers under physiological conditions. Ultimately the cross-linkers described above may be included in all variety of hydrophilic and hydrophobic polymer networks to which the desirable property of degradation is required.

Design of Centro-symmetric Degradable Cross-linkers Based on the Alpha-hydroxy Acids Of importance in hydrogel engineering is the control the structural properties of a random polymeric network. In standard stepwise growth of polymers there is heterogeneity in copolymer composition and dispersity in the molecular weight of the polymer filaments thus making it difficult to precisely control bulk material properties of the polymer network such as crystallinity and mesh size. By engineering homogeneous structures into the polymer structure, usefully tuned macromolecular properties such as biodegradability can be obtained.

Hydrogel networks in the form of colloidal particles which are being explored for use in drug delivery (Kiser et al.) are not biodegradable owing to their carbon-carbon bond containing backbone and their methylene-bis-acrylamide cross-links. This fact initiated the design of a new class of centro-symmetric cross-linking monomers. One of the preferred characteristics of the new material was that it must be easily synthesized. A second preferred characteristic is that the cross-linkers be composed of biocompatible components. The third characteristic which separates this work from all other work in this area is that the biodegradable cross-linker be synthesized to be a single pure molecule and not a mixture. This characteristic should lead to defined biodegradation rates versus the use of a cross-linker mixture as in previous work (Pathak et al.).

Therefore by utilizing classical organic synthesis methodology to synthesize monodispersed degradable sequences into the monomer structure before polymer formation presents an opportunity to carefully control the overall degradation as well as possibly the release rate of entrapped substances. One of the particularly preferred embodiments of these cross-linkers is that they are composed of a symmetrical diacid each acid attached to a biodegradable regions consisting of acids, such as the alpha-hydroxy acids glycolic or lactic acid for example. These portions are then preferably terminated by the monomer methacrylate.

The Monomers

Figure 2:
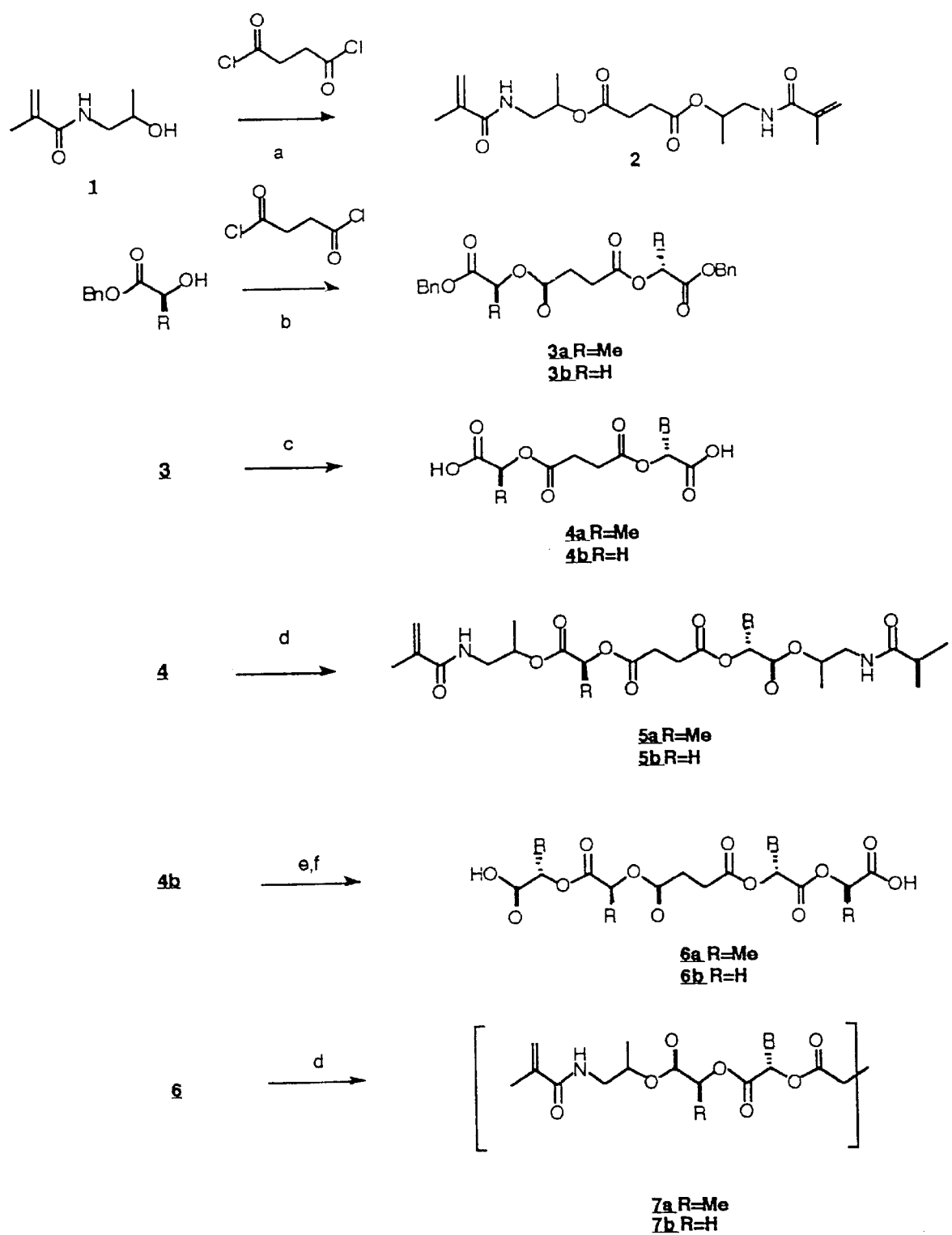
FIG. 2 schematically displays a synthetic method for symmetrical biodegradable cross-linkers such as HPMAL-acSuc 5a, HPMAGlySuc 5b, HPMALacLacSuc 7a, and HPMAGlyGlySuc 7b. Conditions: (a) CH2Cl2, pyridine 0° C.; (b) Pd/C 50 psi H2, i-PrOH; 0° C.; (c) carbonyldiimidazole CDI, DMF, 0° C.; HPMA, rt.; (e) (CDI), DMF, 0° C.; benzyl lactate (6a); benzyl glycolate (6b); (f) Pd/C 50 psi H2, i-PrOH.
Figure 3:
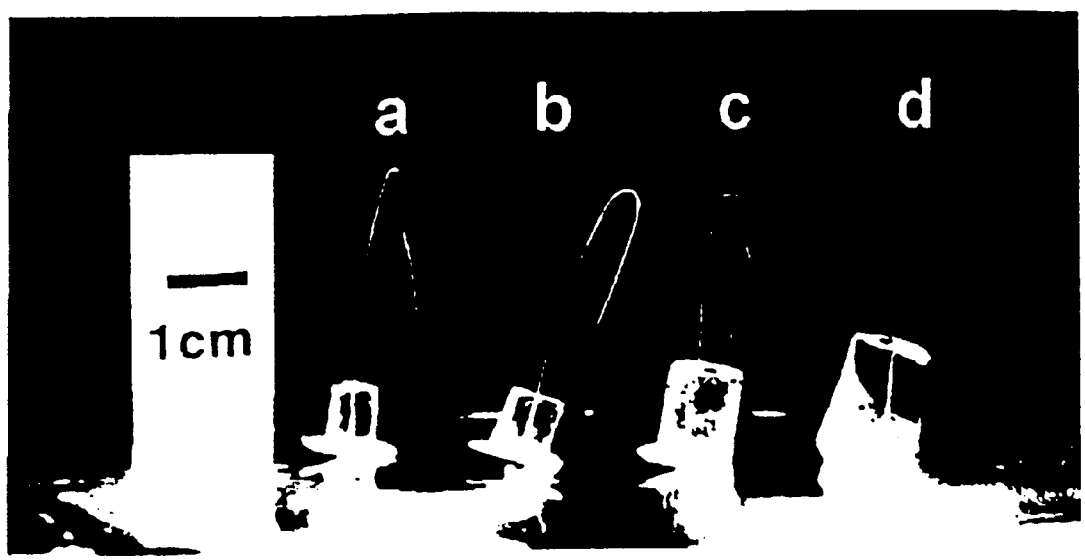
FIG. 3 displays a photograph of biodegradable gels of the same composition with 1.5 mole % cross-linker after incubation in pH 7 phosphate buffer at 37° C. for varying amounts of time. (a) control gel made up of compound 2 after 15 days (b–d) compound 5b after 2, 5 and 15 days, respectively.

The monomers are composed of a central. polyacid as in FIG. 1 and are attached to the degradable region through oxygen, nitrogen, or phosphorous atoms. Structure A shows a monomer having a central diacid region ———, and a degradable region MWW which is then terminated by a reactive polymerizable region ---------X. Structure B is similar and uses the same symbols except that the central core is a triacid symbolized by a T structure. FIG. 2 displays a more specific embodiments of this invention. In structure C, a symmetrical centerpiece (succinic acid) is attached to two degradable regions containing alpha-hydroxy esters. These are then attached to a moiety ($R_2$) which may or may not impart water solubility through the connecting portion labeled Y. Finally, the cross-linker is terminated with vinyl groups. Structure D is again similar to structure C except in this case the monomer is terminated with two nucleophilic moieties which could be used to cross-link preformed polymer chains. These structures are exemplary only. Many more are conceivable by those skilled in the art.

In a preferred embodiment the network begins with a cross-linker containing two equal degradable regions attached to a central diacid and each containing a terminal reactive group. In a particularly preferred embodiment, the core is made of succinic acid, each degradable region is composed of either symmetrical units of glycolic or lactic acid where n in FIG. 1 is between 1 and 5 and the terminal reactive group is a acrylate type moiety where R2 in FIG. 1 is CH(CH3)CH2CO and Y is equal to oxygen.

Central Component

In preferred embodiments the central piece can consist of esters of dicarboxylic acids such as malonic succinic, adipic, sebacic, maleic fumaric acids or even possibly (alpha, omega-(oligo(ethylene glycol)) dicarboxylic acid (alpha, omega-(oligo(propylene glycol)) dicarboxylic acid. Other diacids such as aromatic polycarboxylic acids may also be used. In another embodiment tri-acids such as citric acid or tetra and penta acids such as EDTA and DTPA (possibly as protected derivatives) could also be utilized. Also protected versions of tartaric, citric, aspartic or glutamic acid may be used in certain embodiments.

Biodegradable Component

The biodegradable region is preferred to be hydrolyzable under environmental or in vivo conditions. In the most preferred embodiment the degradable regions will be composed of glycolic or lactic acid domains containing anywhere from one to six members in each oligomeric region attached to the central piece. Other hydroxy esters that may be embodied include: (3-hydroxy butyric acid, 2-hydroxy propanoic acid, and 5-hydroxy caproic acid. Other useful biodegradable regions include amino acids, ortho-esters, anhydrides, phosphazines, phosphoesters and their oligomers and polymers.

Reactive Cross-linking Polymerizable Region

This region is necessary for the invention because it is the chemical functionality terminating the two or more ends of the cross-linker which will chemically bind polymer filaments together. The preferred method of achieving this end is through an acrylate moiety, with polymerization through free radical generation. Free radical generation can be accomplished via thermal, photochemical or redox catalysis initiation systems (Odian). The preferred polymerizable regions for free radical generation are acrylates, vinyl ethers, diacrylates, oligoacrylates, methacrylates, dimethacrylates, and oligomethacrylates. Alternatively another preferred method of cross-linking preformed chains in solution is to attach two or more nucleophiles to the end of the chains which would be reactive with an electrophile attached to the polymer chain. The preferred chemical reactive moieties for this method are carbonate, carbamate, hydrazone, hydrazino, cyclic ether, acid halide, acyl azide, alkylazide, succinimidyl ester, imidazolide, amino groups, alcohol, carbonyl, carboxylic acid, carboxylic ester, alkyl halide, aziridino, nitrile, isocyanate, isothiocyanate, phosphine, phosphonodihalide, sulfide, sulfonate, sulfonamide, sulfate, silane, or silyloxy groups.

Initiators

Several initiation systems for the formation of polymer networks are useful with these compounds, depending on the application and the conditions used.

For generation of polymer slabs either irradiation of vinyl groups with high energy light such as in the UV is a suitable method for initiation. Other preferred methods include the use of thermally activated initiators such as azobisisobutyronitrile or benzoyl peroxide for initiation in water or mixed water/organic solvents, other water soluble alkyl diazo compounds, ammonium persulphate with or without N,N,N',N'-tetramethyethylene diamine.

For generation of particles by emulsion polymerization generation of radicals by thermal initiation is convenient. Generally this is accomplished with water soluble initiators such as ammonium persulphate. Other initiators include the water soluble alkyl diazo compounds.

For generation of polymer networks in vivo the most useful initiation system is photochemical. Photochemical initiation of free radical polymerization involves light activation of a light absorbing compound (a dye), radical abstraction of a hydrogen to generate the initiation radical (usually an amine), and attack of this radical on a vinylic moiety beginning the polymerization. This system preferably requires free radicals to be generated locally and within a short time period, preferably in seconds. Initiation in this system begins with irradiation of light at the appropriate wavelength. The wavelength is chosen to be as close to the absorption maximum of the dye as possible. The preferred light absorbing compounds which will begin the radical generation process are eosin dyes, 2,2'-dimethoxy-2-phenyl acetophenone and other acetophenone derivatives. Other photo redox active dyes include acridine dyes, xanthene dyes and phenazine dyes, for example, acriblarine, rose bengal and methylene blue, respectively. These dyes when photoactivated assume a triplet excited state which can abstract a proton from an amine and thus generate a radical which begins the polymerization. Compounds which act as the initiating radical are amines such as triethanolamine, sulfur containing compounds such as ammonium persulphate, and nitrogen containing-heterocycles such as imidazoles.

Applications for the Cross-linkers

Nature of the Polymer

In the preferred embodiment of this invention, these cross-linkers can be incorporated in biodegradable network polymers that are either hydrophilic or are hydrophobic. Hydrophobic networks will contain less than 5% of the total mass of the polymer network as water. Whereas hydrophilic networks can contain as great as 99% water as the total mass. Hydrophilic network polymers are known as hydrogels to those skilled in the art. Those skilled in the art will generally recognize the polymer structures which are generally considered to be hydrophilic or hydrophobic.

In Vivo Drug Delivery

One preferred application of these materials is in the use of controlled delivery of bioactive compounds. In this method the cross-linker is homopolymerized or copolymerized with other monomer or polymers which may be charged or uncharged. The drug is placed in the polymer network by polymerizing the network around the drug (i.e., by co-dissolving or dispersing the drug with the monomer solution) or by incubating the resulting polymer with a solution of the drug whereby it diffuses into the polymer network. In this embodiment the drug may be anywhere from 1 to 90% by weight of the device. The biologically active compounds can be (but are not limited to) proteins, peptides, carbohydrates, polysaccharides, antineoplastic agents, water soluble linear and branched polymeric prodrugs, particles containing drug, antibiotics, antibodies, neurotransmitters, psychoactive substances, local anesthetics, anti-inflammatory agents, spermicidal agents, imaging agents, phototherapeutic agents, DNA, oligonucleotides and anti-sense oligonucleotides.

An alternative method of producing a biodegradable drug delivery system is through the production of particles. The preferred size range is between 10 nm and 10 $\mu$m. These particles can be produced by emulsion polymerization in water containing a surfactant such as sodium dodecyl sulfate, an initiator such as ammonium persulphate, and cross-linking monomer and co-monomer(s) such as 2-hydroxypropyl methacrylamide, 2-hydroxyethylmethacrylate, acrylic acid, methacrylic acid, methyl methacrylate, methyl acrylate, or other suitable monomers by themselves or in mixtures. Alternatively the particles can be synthesized by precipitation polymerization in organic solvent containing organic soluble initiator such as azobisisobutronitrile and co-monomer(s) such as acrylamide, as 2-hydroxypropyl methacrylamide, 2-hydroxyethyl methacrylate, acrylic acid, methacrylic acid, methyl methacrylate or methyl acrylate by themselves or in mixtures. In this method the preferred route of incorporating drug in the particles is by first synthesizing the particle, followed by purification through washing. The particle is then incubated with drug which is bound to the polymer network by either hydrophilic or ionic forces or by entrapment within the network.

Another method which is well known to those skilled in the art of producing polymer particles includes dissolving the cross-linking monomer, co-monomer, initiator with or with our drug in water and then dispersing this solution in oil. The resulting oil droplets then act as templates for the formation of the gel network. Polymerization is initiated either thermally, chemically or photochemically depending on the monomer system and initiator system. Which combination of systems to use will be obvious to those skilled in the art. The resulting particles can then be sedimented and isolated and purified. This technique is particularly useful for producing larger particles in the 5- to 1000 micron in diameter size range.

Another preferred method for the creation of a drug delivery device is to create a homopolymer network of the cross-linker in organic solvent in the presence of a organic soluble drug. The network is then dried and contains drug dispersed within it. The highly cross-linked network will begin to erode when hydrated and release drug.

Water Absorbents

In this application an important consideration is to copolymerize the biodegradable cross-linker with charged monomers (either negative charges or positive charges or mixtures thereof). Very high charge densities in the polymer network can be obtained by copolymerization of charge monomers into networks (>5 M). The presence of charges in the polymer network require counterions for electroneutrality. These counterions bind water to a lesser or greater extent, depending on their size and polarizabilities. Since the volume of the hydrated gel is equal to the volume of polymer, the volume of water bound to the polymer and the volume of the hydrated ions bound to the polymer, the presence of a large amount of hydrated ions can create a super-water absorbent hydrogel. The molar ratio of cross-linker to other monomers should be kept as low as possible so as to not inhibit the swellability of the network, preferably in the range of 5 mol % or less. The preferred copolymers include methacrylic acid, acrylic acid, acrylic and methacrylic monomers containing sulfate, alkyl carboxylate, phosphate, amino, quaternary amino and other charged groups and their salts. In this application large batches of the degradable network will be synthesized either by dispersion polymerization or in bulk. The material could be synthesized in the presence of a suitable counterion such as sodium for negatively charged filaments or chloride for positively charged filaments. Alternatively the polymer may be formed in its neutral state and then incubated with a suitable acid or base such as hydrochloride in the case of nitrogen containing co-monomers, and soluble metal hydroxides in the case of acidic co-monomers. The most preferred method is to polymerize the cross-linker with the salt form of the co-monomer.

Adhesives

Another use of the monomer is in temporarily binding two surfaces together. The biodegradable cross-linking monomer and co-monomer or just the biodegradable cross-linking monomer itself are mixed together with a solvent and an initiator by itself or with a co-catalyst. The mixture is then spread on the surfaces which are to be adhered, then polymerization is initiated by addition of heat or by light. In the case of light initiation at least one of the surfaces to be adhered must be transparent to the light beam in order for the polymer network to form. The initiation systems described above can be used to this end. Such biodegradable adhesives should have many uses.

Tissue Supports

There is a need for degradable polymers as cell scaffolds in tissue engineering. In this application the tissue scaffold would be synthesized under sterile conditions in a suitable biocompatible buffer. The cross-linking density should be controlled so as to obtain a pore size large enough to allow cell migration. Pore size may be determined by scanning electron microscopy and by using macromolecular probes. A cell suspension containing cells such as, but not limited to, keratinocytes, chrondocytes and osteoblasts, would be injected into the polymer network along with suitable growth factors. The cells would then be allowed to grow within the network. As the cells grow the network around them would degrade. Bioadhesive moieties such as RGD peptide sequence (Arg-Gly-Asp) could be connected to matrix and thereby provide adhesive domains for the growing cells. The timing of the network degradation should coincide with the cells forming their own network (artificial tissue) through inter-cell contacts.

The following examples are presented to describe preferred embodiments and utilities of this invention but are not intended to limit the use or scope of the methods, compositions or compounds claimed in this invention unless otherwise stated in the claims. Taken together, these examples describe the best currently understood mode of synthesizing and incorporating these materials into polymer networks.

The synthesis of the four members of the preferred class of molecules claimed herein are given in FIG. 2. This invention has several advantages over related inventions in this area, including: (1) the cross-linking agents are biodegradable to biocompatible substances, (2) the syntheses are both general and flexible, allowing for a variety of monomeric units to be incorporated, (3) the end groups (e.g., acrylate or hydrazide) can be readily modified to accommodate either condensation or radical-type polymerizations.

EXAMPLE 1

Synthesis of Symmetrical Biodegradable Crosslinker (HPMALacSuc)

Preparation of di(S)-1-[benzyloxycarbonyl]ethyl butane-1,4-dioate (BnLacSuc) (3a). 3a was prepared by reaction of benzyl (S)-(−) lactate (27.0 g, 150 mmol) with pyridine (15.2 mL, 188 mmol), and succinyl chloride (8.21 mL, 75.0 mmol) in dichloromethane (100 mL) at 0° C. with subsequent stirring for 16 hours at 25° C. An additional aliquot of succinyl chloride (1.6 mL, 15 mmol) was then added to ensure complete consumption of benzyl lactate. The reaction was allowed to stir 4 additional hours. After filtering the suspension through activated carbon, the dark solution was washed with 100 mL water, 2–50 mL portions of 1M HCl, 2–50 mL portions of 2–100 mL sat. NaHCO3 and 100 mL brine. The organic phase was then dried over Na2SO4 and concentrated in vacuo to a viscous brown oil. Yield of 3a: 32.3 g (97%). [a]D=−43.2 (c=1.0, CHCl3). Elution through a short column (8.5 cm i.d. by 4 cm) of silica gel (70–230 mesh) using 3:7 ethyl acetate/hexane resulted in a yellow oil of high purity by NMR. 1H NMR (CDCl3): 1.49 (d, 6H, J=7.1 Hz), 2.65–2.72 (m, 4H), 5.08–5.21 (m, 6H), 7.29–7.34 (m, 10H). 13C NMR (CDCl3): 16.63, 28.47, 66.76, 68.68, 76.49, 77.52, 127.91, 128.21, 128.40, 135.13, 170.30, 171.34. Anal. Calcd. for C24H26O8: C, 65.15; H, 5.92. found: C, 65.06; H, 6.02.

Preparation of (2S)-2-{3-[((1S)-1-carboxyethyl) oxycarbonyl]propanoyloxy}propanoic acid (LacSuc) (4a). LacSuc was prepared by hydrogenolysis of BnLacSuc (3a) (10.2 g, 23.1 mmol) over Pd/C (1.0 g, 10% wt. Pd, Degussa type) in 2-propanol (100 mL). The material was placed on a Parr hydrogenator at 50 psi. at 25° C. When hydrogen uptake had ceased, the sample was removed from the hydrogenator, and the Pd—C was then removed by filtration through celite. The solvent was removed in vacuo at 40° C. (16 hours). The crude product was purified by crystallization of its dicyclohexylamine salt as follows: crude 5 (6.4 g, 23 mmol) was dissolved in 50 mL of a toluene/ethyl acetate/ethanol (2:2:1) solvent mixture. Dicyclohexylamine (9.2 mL, 46 mmol) was added to the diacid solution at 0° C. Crystallization was induced by cooling to −10° C. and scratching the sides of the flask. The white solid was washed with 30 mL portions of ethyl ether. Concentration of the mother liquor allowed isolation of a second crop. The first and second crop were combined to give a total yield of 30.2 g [a]D=−26.9, (c=1.0, CHCl3). The dicyclohexylamine salt was dissolved in 5:1 water/ethanol (10 mL) and subjected to strong cation exchange chromatography (BioRad AG 5OW-X4, 200–400 mesh) to regenerate the dicarboxylic acid form. The eluate was lyophilized to remove water/ethanol. The light yellow oil which resulted was taken up in 100 mL dichloromethane/ethyl acetate (5:1) and dried over Na2SO4, to remove residual water. The organic solvents were removed in vacuo, and heating the viscous residue to 65° C. under vacuum (0.5 mm Hg) was required to induce crystallization of the diacid 4a. Yield of 4a: 3.75 g (63%): mp 59–61° C.; [a]D=−54.5, (c=1.0, CHCl3): 1H NMR (CDCl3): 1.54 (d, 6H, J=7.1 Hz), 2.72–2.77 (m, 4H), 5.13 (q, 2H, J=7.1 Hz), 10.97 (br, 2H). 13C NMR (CDCl3): 16.56, 28.51, 68.40, 171.62, 176.28. Anal. Calcd. for C10H14O8: C, 45.81; H, 5.38. found: C, 46.01; H, 5.55.

Preparation of di(1S)-1-{[1-methyl-2-(2-methylprop-2-enoylamino) ethyl]oxycarbonyl}ethyl butane-1,4-dioate (HPMALacSuc) (5a). LacSuc (4a) (2.20 g, 8.3 mmol) was dissolved in dichloromethane (30 mL) and cooled to 0° C. under an argon atmosphere in a three-necked flask equipped with a stir bar and a powder addition funnel. The reaction vessel was then charged with CDI (2.75 g, 17.0 mmol) via the powder addition funnel. Upon addition of the CDI the reaction frothed copiously. The reaction vessel was allowed to warm to 25° C., and then HPMA (2.57 g, 17.0 mmol) was added. The reaction was stirred at 25° C. for 2 hours, and then washed with 1 M NaH2PO4 (2–100 mL), sat. Na2CO3, (10 mL) and brine (10 mL). The dichloromethane phase was then dried over Na2SO4 and concentrated in vacuo to a light yellow, viscous oil. Yield of 5a: 4.08 g (95%). Although the purity was >90% by TLC and NMR, the purity could be improved by flash chromatography. Elution on 300 mL silica gel (230–400 mesh) using 3% methanol/dichloromethane resulted in 3.22 g (75%) of 5a: [a]D=−21.3, (c=1.0 CHCl3) 1H NMR (CDCl3): 1.24–1.29 (m, 6H), 1.47–1.51 (m, 6H), 1.96 (s, 6H), 2.70–2.74 (m, 4H), 3.20–3.38 (m, 2H), 3.57–3.72 (m, 2H), 4.87–5.00 (m, 2H), 5.03–5.16 (m, 2H), 5.33–5.36 (m, 2H), 5.71–5.75 (m, 2H), 6.25–6.55 (m, 2H). 13 C NMR (62.9 MHz, DMSO-d6 several peaks exhibited duality which maybe due to hindered rotation or diastereomers): 16.53, 17.21, 17.37, 18.55, 28.20, 42.99, 54.88, 68.74, 70.17, 70.22, 119.11, 139.83, 139.87, 167.68, 167.83, 169.72, 169.89, 171.27, 171.35. HRMS (FAB+) Calc for C24H27N2O10 (M+H) 513.2448, found 513.2418.

Materials and Characterization

All chemicals were reagent grade and were used without purification unless otherwise noted. 1H NMR and 13C NMR spectra were recorded at 400 and 100.4 MHz respectively on a Varian INOVA-400 spectrometer equipped with a temperature-controlled probe. Abbreviations for NMR data are as follows: s=singlet, d=doublet, m-multiplet, dd=doublet of doublets, t=triplet. Melting points are uncorrected. Coupling constants (J) are reported in Hertz. Chemical shifts are reported in parts per million. 1H shifts are referenced to CHCl3 (7.24) or to DMSO (2.54) and 13C spectra are referenced to CHCl3 (77.14) or to DMSO (40.45). Solvent mixtures are given in volume to volume ratios unless otherwise stated. Flash chromatography was performed on SiO2 Kieselgel 60 (70–230 mesh E. Merck). Mass spectroscopy was performed at the Duke University Mass Spectrometry Laboratory. Optical rotations were obtained using the Na+ 589 nm line at in CHCl3 or acetone using a Perkin-Elmer 241 polarimeter in a 1 dm cell.

THF was used freshly distilled from sodium benzophenone ketyl under nitrogen. 2-propanol was dried by distilling from CaO and storing over 4A molecular sieves. Dichloromethane was distilled from P2O5 and stored over molecular sieves. All other solvents were obtained in their anhydrous state or stored over molecular sieves before use. Hydrogenations were performed on Parr hydrogenator at 30 to 50 psi of hydrogen gas.

EXAMPLE 2

Synthesis of Symmetrical Biodegradable Cross-linker HPMAGlySuc

Preparation of di[benzyloxycarbonyl]methyl butane-1,4-dioate (BnGlySuc) (3b). Compound 3b was synthesized by dissolving benzyl glycolate (15.0 g, 90.3 mmol) and pyridine (7.9 mL, 97 mmol) in 150 mL of CH2Cl2 at 0° C. and adding succinyl chloride (4.7 mL 43 mmol), via a syringe while stirring under an argon atmosphere. The reaction was allowed to warm to room temperature and stir for 3 hours. After 3 hours, TLC (5:95 methanol/CHCl3 Rf=0.5) indicated almost complete reaction, and 0.5 mL of succinyl chloride was added. The reaction was allowed to stir for 12 more hours. The reaction was washed with 2–50 mL of saturated NaHCO3 followed by. 2–50 mL 1M NaH2PO4 and then 1–50 mL of brine. The organic layer was dried over Na2SO4. The crude brown solid was concentrated in vacuo. The compound was purified using flash chromatography on a 7 cm i.d. by 40 cm bed of SiO2 eluting isocratically with CHCl3. Alternatively, the solid could be purified by recrystallization from (1:1 ethyl acetate/hexane). The pure fractions were combined and concentrated in vacuo to yield 3b as a white solid. Yield of 3b: 14.6 g (82%). 1H NMR (CDCl3): 2.77 (s, 4H), 4.65 (s, 4H), 5.17 (s, 2H ), 7.29–7.34 (m, 10H); 13C NMR (CDCl3): 28.71, 61.01 67.21, 128.65, 135.13, 167.58, 171.51. Anal. Calcd. for C22H18O10: C, 59.73; H, 4.10 found: C, 59.64; H, 4.25.

Preparation of 2-{3-[(carboxymethyl)oxycarbonyl] propanoyloxy}acetic acid (GlySuc) (4b). Compound 4b was prepared by dissolving 3b (5.0 g, 11.3 mmol) in 2:1 2-propanol/CH2Cl2 (150 mL) in the presence of 500 mg of Pd/C (Degussa type). The reaction mixture was place on a Parr hydrogenator at 50 PSI for 5 hours, at which time uptake of hydrogen gas had stopped. The reaction was filtered through celite to remove the catalyst and the reaction was concentrated in vacuo resulting in a white solid. The solid was triturated with diethyl ether and dried further. Attempts to further purify this material through the dicyclohexylamine salt resulted in low yields due to liability of this material in water. However, the NMR of the titurated product displayed no extraneous NMR resonances. Yield of 4b 2.54 g (96%): 1H NMR (d6-DMSO): 2.62 (s, 4H), 4.44 (s, 4H), 5.74 (m, 4H); 13C NMR (d6-DMSO): 28.40, 60.61, 169.32, 171.30. HRMS (FAB+) calcd. for C8H10O8 (M+H) 233.0376, found 233.0290.

Preparation of di{[1-methyl-2-(2-methylprop-2-enoylamino)ethyl]oxycarbonyl}methyl butane-1,4-dioate (HPMAGlySuc) (5b). The cross-linker HPMAGlySuc was prepared by adding 4b (3.40 g, 14.5 mmol) to a 100 mL three necked round bottomed flask under an argon atmosphere at 0° C. The reaction vessel was evacuated three times and dry DMF (25 mL) was added to the vessel under pressure. CDI (4.71 g, 29.0 mmol) was added rapidly via a powder addition funnel with vigorous stirring and was accompanied by copious frothing and the formation of the partially soluble diimidazolide. The slurry was allowed to warm to room temperature and HPMA (1) (4.16 g 29.0 mmol), dissolved in 10 mL of DMF, was added to the reaction through a syringe. The reaction was allowed to stir for 15 hours during which time the precipitate dissolved. TLC of the reaction mixture indicated complete conversion of the HPMA (10:90 methanol/CHCl3 Rf 5b=0.55). The reaction was diluted with CH2Cl2 (300 mL) and was washed with 1M NaH2PO4, (2–75 mL), NaHCO3 (2–75 mL) and of brine (100 mL). The organic layer was dried over Na2SO4. The solvent was removed in vacuo (T<35° C.) to yield a light yellow oil. The material was purified by flash chromatography on a SiO2 column (6 cm i.d. by 20 cm) eluting with CH2Cl2 followed by 2-propanol/CH2Cl2. Fractions containing pure product were combined and the solvent removed in vacuo (T<35° C.) to yield a colorless oil. Yield of 3b: 5.83 g (83%). 1H NMR (CDCl3): 1.23 (d, J=6.4 Hz, 6H), 1.92 (s, 6H), 2.74 (s, 4H), 3.21–3.28 (m, 2H), 3.55–3.62 (m, 2H), 4.54 (dd, 4H J1=10 Hz J2=3.2 Hz), 5.01–5.12 (m, 2H), 5.31 (d, J=1.0 Hz, 2H), 5.67 (d, 2H, J=1 H2), 6.15–6.25 (m, 2H); 13C NMR (CDCl$_3$): 17.64, 18.70, 28.51, 28.54, 43.95, 43.01, 61.45, 71.90, 119.92, 119.94, 139.86, 167.42, 167.46, 168.66, 172.026, 172.07. HRMS (FAB+) Calcd for (M+H) C22H33N2O10 485.2057 found, 485.2123.

EXAMPLE 3

Synthesis of Symmetrical Biodegradable Cross-linker HPMALacLacSuc

Preparation of (1S)-1-[benzyloxycarbonyl]ethyl (2S)-2-hydroxy propionate (BnLacLacOH). BnLacLacOH was prepared by the acid catalyzed ring opening of 1-lactide. A 250 mL round bottomed flask was charged with l-lactide (15.0 g, 104 mmol) benzyl alcohol (12.4 g, 114 mmol) and camphor sulfonic acid (139 mg, 624 μmol) along with dry benzene (100 mL). The reaction was refluxed under argon for 36 hours. TLC indicated that the reaction had consumed most of the l-lactide (THF/hexanes/EtOH 45:45:10 Rf lactide=0.1 (phosphomolybdic acid stain)). The reaction was washed with of 200 mM NaHCO3 (2–50 mL), dried over Na2SO4 and the solvent was removed in vacuo. The resultant clear oil was fractionally distilled under high vacuum (30 mtorr) using a vacuum-jacketed Vigreux column. The product was collected in a fraction between 108 and 115° C. Yield of BnLacLacOH: 19.8 g (69%) 1H NMR (CDCl3) 1.40 (d, 3H J=6.8 Hz), 1.49 (d, 3H J=3.8 Hz), 3.00 (br, 1H), 4.28–4.38 (q, 2H J=6.8 Hz), 5.10–5.23 (m, 2H), 7.30–7.4 (m 5H) 13C NMR (CDCl3): 16.79, 20.33, 66.68, 66.82, 67.19, 69.26, 128.20, 128.48, 128.59, 135.05, 170.09, 175.00. HRMS (FAB+) Calcd C13H16O5 (M+H) 253.0998 found 253.1066.

Preparation of (1S)-1-({(1S)-1[benzyloxycarbonyl]ethyl}oxycarbonyl)ethyl(1S)-1-({(1S)-1-[benzyloxycarbonyl]ethyl}oxycarbonyl)ethyl butane-1,4-dioate. BnLacLacOH (4.00 g, 15.9 mmol), pyridine (1.32 mL, 16.4 mmol) was dissolved in dichloromethane (50 mL) and cooled to 0° C. under a N2 atmosphere. To this mixture was added succinyl chloride (0.90 mL, 8.2 mmol) over a period of 20 minutes. The reaction vessel was allowed to warm to 25° C., and was stirred for 3 hours. TLC indicated the reaction had nearly reached completion and an additional aliquot of succinyl chloride was added (0.5 mL, 4.5 mmol). The reaction was stirred for 1 hour more. The reaction was diluted with of CH2Cl2, (50 mL) and poured into water, and washed with 2N HCl (2–50 mL), water (2–50 mL), 2 M NaHCO3, (100 mL) and brine (50 mL). The CH2Cl2 phase was then dried over Na2SO4, and concentrated in vacuo to a bronze-colored oil. Yield of BnLacLacOH: 35.8 g (85%). An analytically pure sample of 9 was prepared by flash chromatography on silica gel (230–400 mesh) using 30:70 ethyl acetate hexane. [a]D=−71.60, (c=1.0, CHCl3); 1H NMR (CDCl3): 1.48 (d, 6H, J=7.0 Hz), 1.50 (d, 6H, J=7.1 Hz), 2.60–2.70 (m, 4H), 5.06–5.24 (m, 8H), 7.28–7.36 (m, 1H). 13C NMR (CDCl3): 16.38, 16.50, 28.36, 66.86, 68.36, 68.87, 127.98, 128.24, 128.37, 134.92, 169.74, 169.83, 171.29.

Preparation of (1S)-1-({(1S)-1[benzyloxycarbonyl]ethyl}oxycarbonyl)ethyl(1S)-1-({(1S)-1-[benzyloxycarbonyl]ethyl}oxycarbonyl)ethyl butane-1,4-dioate (BnLacLacSuc). LacSuc (4a) (19.1 g, 73.0 mmol) was dissolved in CH2Cl2 (75 mL) and cooled to 0° C. under N2 atmosphere. CDI (26.0 g, 161 mmol) was then added to the reaction vessel. Much bubbling of CO2 gas was observed. The reaction vessel was allowed to warm to 25° C., and then benzyl (S)-(−)-lactate (25.7 g, 143 mmol) was added. The reaction was stirred at 25° C. for 1 hour, and then washed with 2N HCl (2–100 mL), water (100 mL), 10% NaHCO3 (2–100 mL), and brine (100 mL). The CH2Cl2 phase was then dried over MgSO4, and concentrated in vacuo to a bronze-colored oil. Yield of BnLacLacSuc: 35.8 g (85%). An analytically pure sample of BnLacLacSuc was prepared by flash chromatography on silica gel (230–400 mesh) using 30:70 ethyl acetate/hexane. [a]D=−71.4, (c=1.0 CHCl3) 1H NMR (250 MHz, CDCl3): 1.48 (d, 6H, J=7.0 Hz), 1.50 (d, 6H, J=7.1 Hz), 2.60–2.70 (m, 4H), 5.06–5.24 (m, 8H), 7.28–7.36 (m, 1H). 13C NMR (62.9 MHz, CDCl3): 16.38, 16.50, 28.36, 66.86, 68.36, 68.87, 127.98, 128.24, 128.37, 134.92, 169.74, 169.83, 171.29. Anal. Calcd. for C30H36O12: C, 61.43; H, 5.84. found: C, 61.47; H, 6.01.

Preparation of LacLacSuc (2a): LacLacSuc was prepared by hydrogenation of BnLacLacSuc (9a) (35.8 g, 60.8 mmol) over 12.9g Pd—C (10% wt. Pd, Degussa type; 6.08 mmol Pd) in 100 mL 2-propanol/ethyl acetate (2:1). Positive hydrogen pressure was maintained using a gas dispersion tube for 4 hours at 25° C. and then under a balloon of hydrogen for 2 days. The Pd—C was then removed by filtration, and the solvent was removed in vacuo. The crude product was purified by crystallization of its dicyclohexylamine salt as follows: Dicyclohexylamine (24.2 mL, 122 mmol) was added to the crude diacid dissolved in 200 mL 50% ethyl acetate/hexane at 25° C. Crystallization was induced by cooling to −78° C. for 16 hours. The white solid was washed with 30 mL portions of 50% ethyl acetate/hexane. Concentration of the mother liquor allowed isolation of a second crop. The first and second crop were combined to give a total yield of 21.4 g ([a]D=42.5, c=1.0, CHCl3). The dicyclohexylamine salt was dissolved in 25 mL water/ethanol (4:1) and subjected to strong cation exchange chromatography (Dowex 5OX4-400) to regenerate the dicarboxylic acid form. The fractions containing the pure diacid were saturated with NaCl and extracted with 3–100 mL portions of ethyl acetate. The combined organic phases were dried over MgSO4, and concentrated in vacuo. The light yellow, viscous oil was then heated to 65° C. under vacuum (0.5 mm Hg) to remove residual solvent. Yield of 6a LacLacSuc: 9.31 g (38%). ([a]D=–86.2, c=1.0, CHCl3) 1H NMR (250 MHz, CDCl3): 1.55 (d, 6H, J=7.1 Hz); 1.56 (d, 6H, J=7.1 Hz); 2.70–2.80 (m, 4H); 5.09–5.22 (m, 4H); 11.07 (b, 2H). 13C NMR (62.9 MHz, CDCl3): 16.44, 28.42, 68.50, 170.00, 171.61, 175.75.

Preparation of HPMALacLacSuc (7a). LacLacSuc (2.01 g, 4.92 mmol) was dissolved in 10 mL dichloromethane and cooled to 0° C. under N2 atmosphere. The reaction vessel was then charged with carbonyldiimidazole (1.78 g, 11.0 mmol). Much bubbling of CO2 gas was observed. The reaction vessel was allowed to warm to 25° C., and then HPMA (1.43 g, 10.0 mmol) was added. The reaction was stirred at 25° C. for 2 hours, and then washed with 3–10 mL portions of 5% citric acid solution, 10 ml water, 10 mL 10% NaHCO3, and 10 mL brine. The dichloromethane phase was then dried over MgSO4, and concentrated in vacuo to a light yellow, viscous oil. Yield of 7a: 2.55 g (79%). Although the purity was >90% by TLC and NMR, the purity could be improved by flash chromatography. Elution on 400 mL silica gel (230–400 mesh) using 3% methanol/dichloromethane resulted in 2.20g (68%) of HPMALacLacSuc (10a). ([a]D=–24.9, c=1.0, CHCl3) 1H NMR (250 MHz, CDCl3): 1.23 (d, 6H, J=6.4 Hz); 1.39–1.54 (m, 12H); 1.92–1.93 (m, 6H); 2.63–2.78 (m, 4H); 3.18–3.37 (m, 2H); 3.55–3.67 (m, 2H); 4.91–5.11 (m, 6H); 5.29–5.32 (m, 2H); 5.68 (d, 2H, J=9.5 Hz); 6.28–6.33 (m, 2H); 13C NMR (62.9 MHz, CDCl3; several peaks exhibited duality which is due to diastereomers): 16.23, 16.44, 16.50, 17.11, 17.19, 18.31, 28.30, 43.41, 43.63, 68.34, 68–51, 69.58, 71.24, 71.36, 119.47, 119.60, 139.40, 139.49, 168.20, 168.38, 169.46, 169.89, 170.16, 170.45, 171.26.; HRMS(FAB+) Calcd MH+ C30H44N2O14 657.2839, found 657.2849.

EXAMPLE 4

Synthesis of Symmetrical Biodegradable Cross-linker HPMAGlyGlySuc

Preparation of di({[benzyloxycarbonyl]methyl}oxycarbonyl)methyl butane-1,4-dioate (BnGlyGlySuc). GlySuc (4b) (3.50g 14.95 mmol) was dissolved in CH2Cl2 (30 mL) and anhydrous DMF (60 mL) and cooled to 0° C. under argon atmosphere in a three necked flask equipped with a stir bar and a powder addition funnel. The reaction vessel was then charged with CDI (4.85 g, 30.0 mmol) via a powder addition funnel. Upon the addition of the CDI the reaction frothed copiously. The insoluble diimidazolide formed a thick precipitate. The reaction vessel was allowed to warm to 25° C., and then benzyl glycolate (3.82 mL, 30.0 mmol) was added via a syringe in anhydrous DMF (10 mL). The reaction was allowed to run overnight at 25° C. As the reaction proceeded, the reaction mixture slowly became less viscous. The reaction was diluted with CH2Cl2 (500 mL) and was washed with 1M NaH2PO4 (2–100 mL), NaHC3O3 (2–100 mL), and brine (100 mL). The organic layer was dried over Na2SO4 and the solvent was removed in vacuo yield of 4b: 7.67 g 98% (a light yellow crystalline solid). The compound was purified by flash chromatography on a 4.5 cm i.d. by 12 cm column over silica gel. The sample was loaded in 2:1 CH2Cl2/hexanes (100 mL) eluted with of the same (200 mL), of CH2Cl2 (200 mL), of 1:99 THF/CH2Cl2 (200 mL), and finally with THF/CH2Cl2 (3:97). The fractions containing pure product were combined and the solvent removed in vacuo to yield 26 as a pure crystalline solid. Yield of 4b: 6.57 g (83%). 1H NMR (MHz, CDCl3): 2.78 (s, 4H), 4.71 (s, 4H), 4.73 (s, 4H), 5.18 (s, 4H), 7.33–7.39 (m, 10H); 13C NMR CDCl3) 28.65, 60.66, 61.21, 67.42, 128.55, 128.74, 128.78, 135.00, 167.03, 167.22, 171.40; Anal. Calcd. for C26H22O14 C, 55.92; H, 3.97; Found: C, 55.64; H, 4.01.

Preparation of 2-{2-[3-({[Carboxymethyl)oxycarbonyl]methyl}oxycarbonyl)propanoyloxy]acetyloxy}acetic acid (6b). Compound 6b was prepared by suspending 4b (4.58 g, 8.61 mmol) in 1:1 2-propanol/CH2Cl2 (250 mL) in the presence of Pd/C (2.0 g, Degussa type). The reaction mixture was placed on a Parr hydrogenator at 50 PSI for 18 hours at which time uptake of hydrogen gas had stopped. The reaction was filtered through celite to remove the catalyst, and the solution was concentrated in vacuo, resulting in a white solid. The solid was titurated with diethyl ether, and dried further yielding a white solid. Attempts at purification by recrystallization of the dicyclohexylamine salt resulted in complex mixtures upon trying to remove the amine by semi-aqueous ion exchange. This was likely due to the instability of this compound. However the NMR of the titurated product was adequate with a purity >95%. Yield of 6b: 2.87 g (93%): 1H NMR (d6-DMSO): 2.80 (s, 4H), 4.66 (s, 4H), 4.77 (s, 4H), 13C NMR (d6-DMSO): 29.31, 61.34, 61.91, 167.92, 169.57, 171.97. HRMS (FAB) Calcd for (M–H) C12H13O12, 349.0485 found 349.0403.

Preparation of di[({[1-methyl-2-(2-methylprop-2-enoylamino)ethyl]oxycarbon-yl}methyl)oxycarbonyl] methylbutane-1,4-dioate (HPMAGlyGlySuc) (7b). The cross-linker HPMAGlyGlySuc was prepared by adding 6b (1.50 g, 4.28 mmol) to 100 mL three-necked round bottomed flask under an argon atmosphere at 0° C. The reaction vessel was evacuated three times and dry 1:1 DMF/CH2Cl2 (35 mL) was added to the vessel under pressure. The CDI (1.39 g, 8.57 mmol) was added rapidly with vigorous stirring via a powder addition funnel and was accompanied by frothing and the formation of the insoluble diimidazolide. The slurry was allowed to warm to room temperature and HPMA (1.23 g, 8.57 mmol) dissolved in DMF (10 mL) was added to the reaction through a syringe. The reaction was allowed to stir for 10 hours during which time the precipitate dissolved. TLC of the reaction mixture indicated complete conversion of the HPMA (10:90 methanol/CHCl3 Rf 5b 32 0.73). The reaction was diluted with CH2Cl2 (200 mL) and was washed with 1M NaH2PO4 (2–50 mL), NaHCO3 (2–50 mL) and brine (100 mL). The organic layer was dried over Na2SO4. The solvent was removed in vacuo (T<35° C.) to yield a clear oil. The material was purified by flash chromatography on a 6 cm i.d. by 20 cm silica gel column eluting with CH2Cl2 followed by 3:97 2-propanol/CH2Cl2. Pure fractions were combined and the solvent removed in vacuo (T<35° C.) to yield a colorless oil. Yield of 7: 2.08 g (81%): 1H NMR CDCl3): 1.23 (d, 6H J=6.3 Hz), 1.89 (s, 6H), 2.73 (s, 4H), 3.21–3.30 (m, 2H), 3.53–3.62 (m, 2H), 4.524.8 (m, 8H), 5.01–5.17 (m, 2H), 5.28 (s, 4H), 5.64 (s, 4H), 6.23–6.35 (b, 2H), 13C NMR °CDCl3): 17.45, 18.62, 43.80, 60.64, 61.54, 72.12, 119.74, 139.84, 166.75, 167.49, 168.67, 171.50. HRMS (FAB+) Calcd for C26H36N2O14 (M+H) 601.2167 found 601.2219.

EXAMPLE 5

Synthesis of Degradable Hydrogels with TMED Initiation

Biodegradable hydrogels are synthesized by free radical polymerization of the biodegradable cross-linkers and other monomers described herein using the APS/TMED couple.

The vinyl groups on the terminus of the cross-linking structure can be used to form a gel network structure. Gels were synthesized using the ammonium persulphate (APS) N,N,N',N'-tetramethylethylenediamine (TMED) couple as the free-radical initiator system. This system proved very useful in the synthesis of clear isotropic gels, without having to degas the polymerization reactions. The gels in this section were made at a mole feed ratio of 1.5 mole % cross-linker, as a copolymer with 98.5 mole % HPMA. Before the gels were polymerized, three 1.0 mL plastic syringes to be used as a slab gel template were silylanized by briefly incubating them in a heptane solution containing Sigmacote and oven drying at 90° C.

Also, three 8 cm lengths of 25 gauge tungsten wire were silylanized for use in the gel making process and each was threaded through 7 mm Suba Seal rubber septa. The procedure to form gels was as follows: A 7 mL test tube was charged with HPMA (2.115 g, 14.8 mmol [HPMA] final ~5 M), the oily compounds (HPMAGlySuc) was adsorbed to the end of a tarred spatula (109.0 mg, 0.225 mmol, [XL] final=0.075 M). The end of the spatula was placed in the test tube and 1.5 mL of DI water was added to the mixture. The cross-linker was dissolved in the mixture by rapid rotation of the spatula and gentle bath sonication.

The dissolution of the HPMA has a negative heat of solution but the mixture should not be warmed above room temperature. To this solution was added a solution of APS in water (99 mg, 0.438 mmol, 166 μL of a 2.63 M solution, [APS] final=0.143 M). This was again agitated until homogeneous. To this mixture was added TMED to initiate the polymerization (49 mg, 0.429 mmol, 204 μL of a 2.10 M solution of TMED adjusted to pH 7 with HCl). In this preferred embodiment the concentration of TMED must be approximately 0.15 M or greater. It was important to control the pH of the TMED because TMED solutions in water are basic enough to cause significant degradation of the hydrolytically reactive cross-linker. Immediately after the TMED was added the mixture of monomers and APS was vigorously mixed on a vortexer for 15 seconds and then drawn into the 1.0 mL plastic syringes by plunger aspiration. The syringe acts as a mold for gel formation. The syringes were inverted and the tungsten wires were inserted into the gel through the opening so that it runs through the center of the forming 1.0 mL gel: cylinder.

The wire was held in place by a septa which was placed over the tip of the syringe, as the solution polymerized. This formed a hole in the center of the cylinder, which was later used as a place to insert a wire hanger for the initially brittle and finally fragile gel, in order to measure its swelling and degradation kinetics as a change of mass with time. Gelation occurred within one to five minutes and the syringe was allowed to sit for 4 hours at room temperature. At this point the wire was removed from the center of the solid and the end of the plastic syringe was removed with a razor blade. The plunger was then used to extrude the gel from the syringe in 100 μL increments which were cut into small cylinders as they hung out from the end of the syringe. The gels were then placed on tarred wire holders and the initial mass of the assembly was determined. The resulting clear isotropic gels had the composition of poly(HPMA-co-HPMAGlySuc) 98.5:1.5. The gels were then incubated in pH 5, 100 mM sodium acetate buffer for 24 hours. They were then charged into vials of differing pH to study the degradation kinetics.

The gels of the four different compositions contained the following amounts of cross-linkers:

| Compound | MW | Mole % | XL moles | Mass (mg) |
|---|---|---|---|---|
| HPMASuc | 366.38 | 0.015 | 2.25E-04 | 82.4 |
| HPMALacSuc | 512.5 | 0.015 | 2.25E-04 | 115.3 |
| HPMAGlySuc | 484.51 | 0.015 | 2.25E-04 | 109.0 |
| HPMAGlyGlySuc | 600.58 | 0.015 | 2.25E-04 | 135.1 |

EXAMPLE 6

Synthesis of Biodegradable Hydrogel Using AIBN Thermal Initiation

To a 10 mL round bottomed flask was charged HPMA-LacLacSuc (60.75 mg, 125 mol) and azobisisobutryonitrile (free radical initiator) (4.0 mg). To this was added 1.0 mL of a 1:1 methanol:water mixture. The contents were dissolved and degassed under N2 for 0.5 hours followed by 5 minutes in a bath sonicator under a stream of N2. The mixture was charged in 300 ml aliquots into 36×50 mm glass tubes which have been evacuated and capped with rubber septa. The tubes were placed in a 60° C. bath overnight. The next morning the polymer gel had formed. It was removed from the glass tube under vacuum and cut into 2×5 mm disks. The disks were incubated in water for two days. The water was changed at 8 hour intervals to remove any water soluble monomer or reaction byproducts.

EXAMPLE 7

Degradation of Biodegradable Hydrogels
Measuring the Degradation of the Gel Network The gels were placed in 15 mL vials containing 10 mL of buffers. The masses of wire holders were determined before the gels were placed on them. The original mass of the gel in its relaxed state was also known by subtraction from the total mass of the assembly. The original dry mass of the gel was determined by drying three gels in their relaxed state from each composition and determining the dry mass of the gel. These values were then used to calculate the inverse of the volume fraction of polymer in the gel (Qv) respectively, using the densities of the polymer and water. The incubation solutions were changed each time the gel was weighed. The gels were incubated in a gyratory water-bath shaker (New Brunswick Scientific, New Brunswick, N.J.). The temperature was regulated to be 37±2° C. and the shaker was set to 30 rotations per minute.

Explanation of the Order of the Rates of Degradation for Different Cross-linkers Hydrogels are cross-linked structures composed of elastic networks of water-soluble polymers. The maximum degree of swelling is limited by the network elasticity. So as the gel's network structure degrades the cross-link density decreases and the network becomes more elastic. This allows the network to swell further as it imbibes more water. This swelling results in a increase in the volume fraction of water and a corresponding decrease in the volume fraction of polymer. The property of the change of volume of the polymer network can be measured by weighing the gel at different time points.

Since the swelling is related to network cross-link density by weighing the macroscopic gels at various times throughout their swelling one can obtain information about the change in cross-link density and thus the rate of degradation.

The cross-linkers in the gel degrade hydrolytically by the action of the two hydrolytically active components of water:

the hydronium and hydroxide ions. Therefore, the rate of degradation is strongly dependent on pH.

Figure 4:
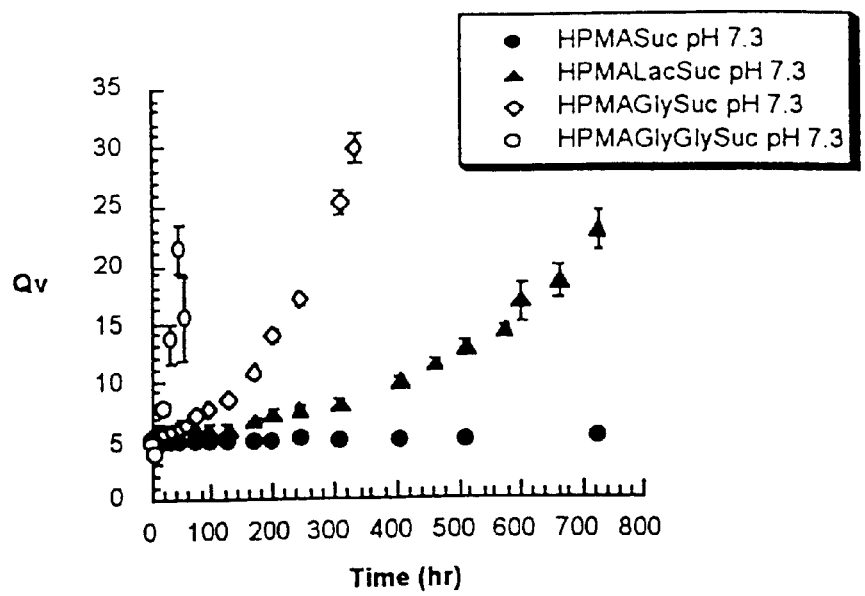
FIG. 4 displays the degradative swelling of HPMA-co-XL gels made from 4 different cross-linkers in pH 7.3 buffer; 100 mM phosphate buffer; 1=200 mM at 37° C. The cross-linker labeled HPMASuc is non-degradable.
Figure 5:
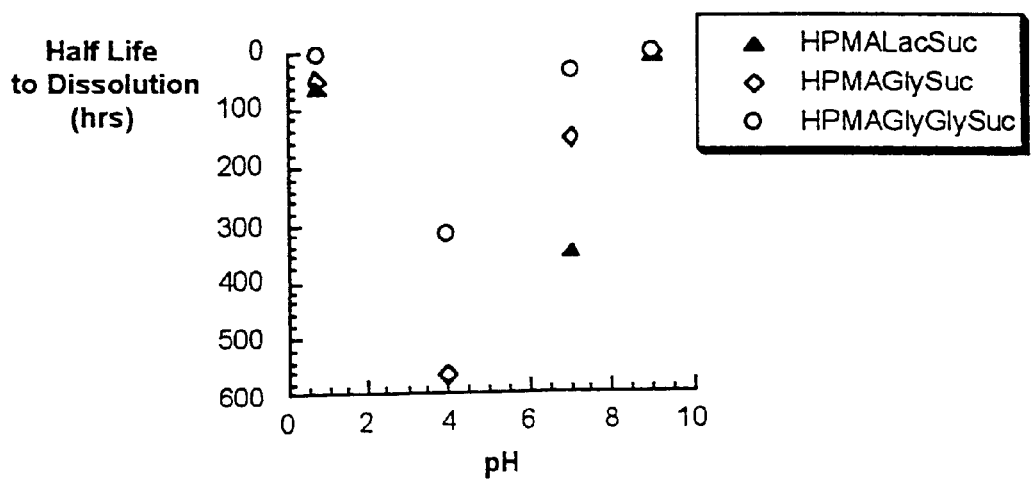
FIG. 5 displays a plot of the half-life to dissolution versus pH for three different degradable cross-linkers studied at 37° C.

HPMALacSuc is electronically similar to HPMAGlySuc 5b yet the lactic ester shows slower degradation than the glycolic. This is because the lactic ester has a methyl group to the carbonyl where the first step of ester hydrolysis takes place, and is sterically hindered in 5a than 5b. HPMAGlyGlySuc 5b shows the fastest hydrolysis and swelling kinetics with complete degradation after about 5 days (See FIGS. 4 through 6).

Moreover, since we are not measuring the rate of hydrolysis of individual bonds but measuring the swelling which comes about as a result of cleaving the connection between two polymer chains, the concentration of cleavable sites comes into play. Therefore, when comparing gels composed of 5b and 7b at the same cross-link density, compound 5b has four potential sites of cleavage and 7b has six. This increased concentration of cleavable sites may result in a difference in swelling rate depending on the relative microscopic rate constants for hydrolysis of the different bonds making up the cross-linker.

Synthesis of the Control Cross-linker HPMASuc

Preparation of the control non-degradable cross-linker bis-1-methyl-2-(2-methylprop-2enoylamino)ethyl-1,4-butanedioate (HPMASuc) (2). To a solution of HPMA (4.00 g, 27.9 mmol), DMAP (340 mg, 2.8 mmol) and Na2CO3 (3.26 g, 30.7 mmol) in CH2Cl2 (100 mL) at 0° C. was added succinyl chloride (1.54 mL, 13.97 mmol) dropwise. The reaction was allowed to warm to 25° C. and stir for 8 hours at which time another aliquot of succinyl chloride was added (0.61 g, 4 mmol). The reaction was allowed to stir for another 4 hours. The reaction mixture was poured into 50 mL of water and filtered through activated carbon. The mixture was then washed with 1 M NaH2PO4 (50 mL), sat. NaHCO3 (50 mL) and brine (100 mL). The organic phase was then dried over Na2SO4, and concentrated in vacuo to a tan residue. This was purified by flash chromatography in 15:85 2-propanol/CHCl3 on a 3 i.d. by 20 cm column. Yield of 2 3.51 g (68%): mp 103–105° C., 1H NMR °CDCl3): 1.24 (d, 6H, J=6.3 Hz); 1.93 (d, 6H, J=0.6 Hz), 2.54–2.65 (m, 4H), 3.31–3.38 (m, 2H), 3.52–3.60 (m, 2H), 4.98–5.05 (m, 2H), 5.31 (d, 2H, J=0.4 Hz), 5.66 (s, 2H), 6.23 (b, 2H). 13C NMR °CDCl3); (several peaks exhibited duality which is most likely due to diastereomers) 17.48, 18.51, 29.38, 43.81, 43.87, 70.48, 70.62, 119.50, 119.56, 139.78, 168.48, 172.24. Anal. Calcd. for C18H28N2O6: C, 58.68; H, 7.65; N, 7.60. found: C, 58.71; H, 7.72; N, 7.48.

EXAMPLE 8

Release of a Soluble Macromolecule from a Degrading Network and Degradation of a Polymer Network Labeled with a Chromophoric Agent Gels were formed by the same method as above, but in this case other compounds were included during the preparation of the gels to study the release of small molecules from the network. In one case, the network itself was labeled with a polymerizable derivative of tetramethyl rhodamine (TMRAHMAm) in order to show the release (degradation) of the network itself (see FIG. 6). In the other case fluorescent rhodamine labeled albumin (Molecular Probes, Eugene Oreg.) was included in the uncharged network to show diffusive release of a macromolecule from the network (see FIG. 7).

To a 3 mL test tube was charged TMRAHMAm (3.0 mg, 5.0 µmol; 30 µL of a 100 mg/mL solution in CHCl3) which was then placed under a 7 mtorr vacuum for 3 hours. To another 3 mL test tube, 4.5 mg of 5+(6) carboxytetramethylrhodamine labeled albumin (Molecular probes) was added. To a third 7.0 mL test tube HPMA was added (1.692 g, 11.8 mmol, [HPMA] final ~5 M), the oily compound 7b (HPMAGlyGlySuc) was adsorbed to the end of a tarred spatula (108.0 mg, 180 µmol, [XL]final=0.075 M). The end of the spatula was placed in the test tube and 1.2 mL of DI water was added to the mixture.

The cross-linker was dissolved in the mixture by rapid rotation of the spatula and gentle bath sonication. HPMA has a negative heat of solution but the mixture should not be warmed above room temperature. To this solution was added a solution of APS in water (80 mg, 0.350 mmol, 79 µL of a 2.63 M, [APS]final=0.143 M). This was again agitated until homogeneous. This viscous mixture was separated into 3–890 µL aliquots. One was mixed with the polymerizable dye (TMRAHMAm) and the other with fluorescent albumin. All resulting monomer mixtures were thoroughly homogenized. To each of these three 890 µL mixtures was added an aliquot of TMED to initiate the polymerization (13.2 mg, 114 µmol, 54 µL of a 2.10 M solution of TMED adjusted to pH 7 with HCl, 244 mg TMED freebase/mL).

All mixtures were mixed for 15 seconds and then placed in the syringe template, with each solution having a final solid volume of about 850 µL. The gels were then allowed to polymerize for 4 hours after which time they were extruded and cut into slices. The gels were weighed, attached to wires and were placed in separate vials for the release studies. The dye labeled gels were incubated in water for two days to allow any unreacted monomer to diffuse out of the network. The gels were placed in 15 nL of buffer solutions at pH 4, 7, and 9. All solutions were incubated at 37° C. on a temperature-regulated orbital-shaking bath at 30 rpm.

Gels were suspended in buffers of different pH's: All buffers were adjusted to the same ionic strength. The release of the rhodamine labeled albumin and the rhodamine labeled HPMA was monitored at 550 nm. 750 µL of the sample was removed from the vial and periodically measured on a spectrophotometer. Release values were normalized to the maximum amount released.

Explanation of the Release Data

The examination of the release of macromolecules entrained in the polymer network provides another way to study the performance of these materials. In this section, the degradation of the network is ascertained by analysis spectrophotometrically through the release of the HPMA polymer backbone itself by labeling it with the polymerizable dye TMRAHMAm. Moreover, the release of a model macromolecular solute (TMRA-albumin, molecular weight of ~66,000 Da.) from the network is measured spectrophotometrically.

Figure 6:
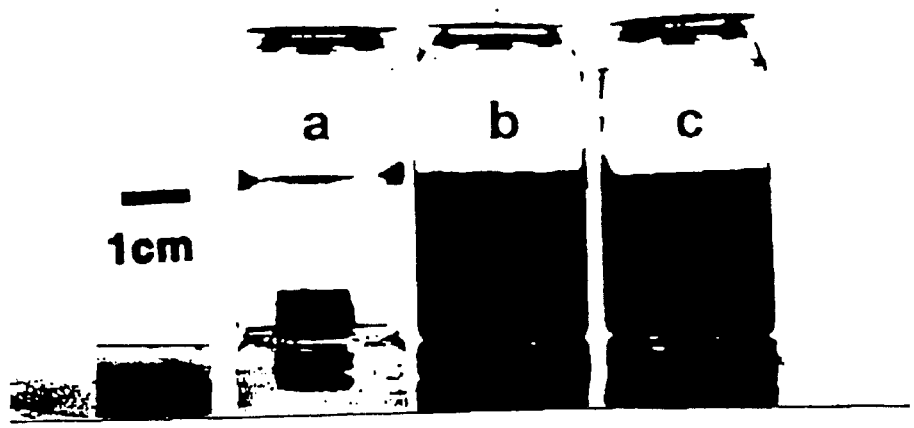
FIG. 6 displays a photograph of p (HPMA) degradable gels with 1.5 mole % cross-linker and containing a deep red fluorescent dye—thus the dark color—after incubation in pH 7 phosphate buffer at 37° C. for varying amounts of time. (a) control gel made from compound 2 after 15 days (b and c) compound 7b after 4, 8 days respectively.
Figure 7:
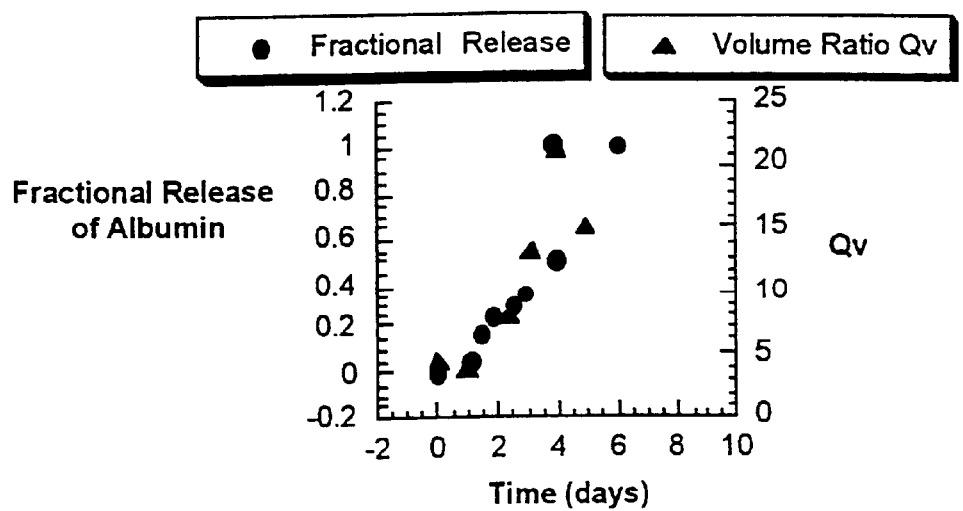
FIG. 7 displays a plot comparing the swelling response and the release of tetramethyl rhodamine labeled albumin from the degradable gel network for HPMAGlyGlySuc 7b at pH 7.3 at 37° C.

FIG. 6 displays a photograph of three different gels in pH 7.3 buffer made with HPMASuc, HPMAGlyGlySuc (4 days) and HPMAGlyGlySuc (8 days), which were co-polymerized with the chromophoric label and HPMA. FIG. 6 displays not only the different degrees of swelling but also the release of rhodamine labeled HPMA into the solution at a given time versus control. FIG. 7 shows the release curve for rhodamine labeled HPMA polymer backbone as well as the corresponding swelling data. The release of rhodamine labeled HPMA largely occurs to the greatest extent at the onset of complete degradation of the polymer. In contrast to the release of the polymer backbone, the release of the globular macromolecule BS albumin more closely follows the swelling of the network.

EXAMPLE 9

Synthesis of Anionic Slab Gels and Loading of DX (Doxorubicin)

Synthesis of Gels Containing Methacrylic Acid

The gels in this section were made at a mole feed ratio of 1.45 mole percent cross-linker as a copolymer with HPMA 95.4 mole % and methacrylic acid sodium salt 3.18 mol%. Before the gels were polymerized, three 1.0 mL plastic syringes to be used as a slab gel template were silylanized with Sigmacote by briefly incubating them in the heptane solution and oven drying at 90° C. (see 1—1). Also, three 8 cm lengths of 25 gauge tungsten wire. The procedure to form gels is as follows: to a 7 mL test tube is charged HPMA (564.1 mg, 0.00394 mol, [HPMA] final ~5 M), the cross-linker (6.00E-05 mol, [XL] final=~0.075M) and the sodium salt of methacrylic acid (42 mg 3.89E-04 mol) are charged into the same vial with the HPMA and 0.4 mL of DI water is added to the mixture. The components of the mixture are dissolved by agitation and gentle bath sonication at 15° C. The dissolution of the HPMA is retarded by its negative heat of solution but the mixture should not be warmed above room temperature. To this solution is added 44.4 µL of a 2.63 M solution of (APS) in water (27 mg, 1.17E-04 mol, [APS]final=0.143M). This is again agitated until homogeneous. To this mixture is added 55 µL of a 2.10 M solution of TMED to initiate the polymerization (13.3 mg, 1.14E-04 mol, TMED solution adjusted to pH 7). It is important to control the pH of the TMED because TMED solutions in water are basic enough to cause significant degradation of the hydrolytically reactive cross-linker. Immediately after the TMED is added the mixture of monomers and APS is vigorously mixed on a vortexer for 15 seconds and then drawn into the 1.0 mL plastic syringes by plunger aspiration which acts as a mold for the forming gel (see above for a description of gel processing).

For gels of the three different compositions synthesized the following amounts of cross-linkers were used in addition to the materials described above.

| Compound | MW | Mole fraction | Moles | Mass (mg) |
| --- | --- | --- | --- | --- |
| HPMASuc | 366.38 | 0.0136 | 0.00006 | 22 |
| HPMAGlySuc | 484.51 | 0.0136 | 0.00006 | 29 |
| HPMAGlyGlySuc | 600.58 | 0.0136 | 0.00006 | 36 |

The gels were cut into approximately equal volumes (100 µL, ~100 mg) and the unloaded masses were determined for the gels in the rubbery state. Each gel was placed in 1.9 mL of a 2.0 mg/ml solution of doxorubicin hydrochloride which was buffered to pH 7.4 with 5 mM TRIS buffer. The gels were agitated with the solution for 4 days at room temperature on a temperature-regulated orbital-shaking bath at 30 rpm. As the red doxorubicin was taken up into the gels the gels became red. The solution around the gels became depleted of doxorubicin due to the ion exchange of doxorubicin for the sodium counterions.

EXAMPLE 10

Method for Making a Biodegradable Water Absorbant Device

As discussed earlier the preferred embodiment of a network polymer for use as a degradable water absorbent will include ionomeric monomers which bring ions and water into the gel network. Below is a description of the method to make a highly charged gel of these cross-linkers.

To a 5 mL test tube was charged acrylic acid (675 µL, 9.85 mmol), water (1120 µL) and HPMAGlySuc (73 mg, 0.15 mmol) (5b). The cross-linker was weighed into the mixture as described earlier. The mixture was homogenized and APS was added (66.6 µL, 0. 175mmol) from a 2.43 M solution in water. This solution was again mixed. To this solution was added TMED (137 µL, 0.287 mmol) from a 2.10 M pH 7.0 solution in water. The mixture was vortexed rapidly for 15 seconds and the polymerizing solution was charged into two 1.0 mL syringes that acted as a mold for the polymerization. The syringes were allowed to sit for four hours. The gel was removed from the syringe and cut into pieces (~100 µL cylinders). The mass of the cylinder was recorded and placed in a 20 mL vial containing 18 mL of PBS at pH 7.4. The gels were incubated overnight with buffer. The next day the buffer was changed twice in order to keep a constant external pH as the gel was charged. After incubating in PBS for 3 days the gel has swollen with water to approximately 20 times the total initial polymer volume.

The salt form of the gel will be synthesized and the gel material processed into smaller pieces either before or after drying. The dry gel pieces would then be incorporated as one component in an absorbable layer of the absorbent device. Generally the pieces should to small so as to increase the surface area of the gel and therefore to increase the rate at which water would be absorbed by the gel material.

EXAMPLE 11

General Method for Synthesizing the Cross-linker

Those skilled in the art of organic synthesis will be aware of the general considerations in designing cross-linkers of this class. Generally if any alcohol groups are present in the poly-acids used they must be protected unless it desired that they react with the activated acids to be used in the formation of the oligo-ester. Generally the synthesis must be performed under anhydrous condition except when performing acid or base washes of water immiscible organic solvents where the cross-linker or intermediate largely partitions into the organic phase. If the materials are to be used in an aqueous environment it is generally best to keep the acid in the anionic form only a few units away from its pKa. This is due to the well-known effect of inhibition of attack of hydroxide by negatively charged electrophiles. In the most preferred cases the cross-linkers are constructed by adding a protected degradable piece to a polyacid. In a preferred embodiment the degradable piece contains a nucleophilic moiety and a protected acidic moiety, e.g. benzyl lactate. The protecting groups are removed under appropriate conditions known to those skilled in the art. The activation and reaction with a protected bifunctional degradable molecule can be repeated on the molecule as many times as desired. Alternatively, the final step of the synthesis can be accomplished by terminating the molecule with reactive groups that are later used to cross-link polymer filaments. The preferred embodiment of the protecting group are groups that can be removed under neutral anhydrous conditions such as the benzyl protecting group. The next preferred protecting groups are ones that can be removed with anhydrous acids or bases such as the BOC or MEM protecting groups.

EXAMPLE 12

Preparation of HydLacSuc (8)

Preparation of di[N-carbobenzoxy-N'-hydrazidooxycarbonyl]ethyl butane-1,4dioate (BnHydLacSuc). To a 25 mL round-bottomed flask was charged 4a (262 mg, 1.00 mmol), THF (2.0 mL), and pyridine (162 µL, 2.00 mmol). The flask was placed on an ice bath and to tile reaction was added isobutyl chloroformate (260 µL, 2.0 mmol). The reaction was allowed to stir and carbobenzoxyhydrazide was added (380 mg, 2.3 mmol). The reaction was allowed to stir overnight. The white solid was dissolved in ethyl acetate and washed with 1M HCl (2–5 mL), water (5 mL) and saturated NaHCO3 (5 mL). The organic layer was dried over MgSO4. The solvent was removed in vacuo resulting in a white solid. Yield of BnHydLacSuc: 392 mg (62%).

Preparation of di[N-hydrazidooxycarbonyl]ethyl butane1,4-dioate (HydLaeSuc) (8). To a 5 mL pressure tube was BnHydLacSuc (279 mg, 0.5 mmol), Pd—C (Degussa Type, 10% Pd, 50% H2O) (600 mg) and cyclohexene (1.25 mL, 12.5 mmol) and MeOH/DMF (1:1, 1.25 mL). The reaction was heated to 60° C. for 3 hours. Evolution of CO2 was observed. The Pd—C was removed by filtration and the solvent was removed in vacuo resulting in an oil

EXAMPLE 13

Preparation of HEMAGlyAdp

Preparation of di[benzyloxycarbonyl]methyloctane-1,8-dioate (BnGlyAdp). Compound BnGlyAdp was synthesized by methods similar to those described for BnGlySuc, compound 3b, by dissolving benzyl glycolate (9.08 g. 54.6 mmoles) and pyridine (4.42 mL., 54.6 mmoles) in 150 mL CH2CH1 at 0° C. and adding adipoyl chloride (5.00 g, 27.3 mmoles) via a syringe while stirring under nitrogen atmosphere. The reaction was allowed to warm to room temperature and stir for 5 hours. After 5 hours, TLC (5:95 methanol/CH2Cl2 Rf=0.63) indicated almost complete conversion, and 0.1 mL of adipoyl chloride was added. The reaction was allowed 12 more hours. The medium was then cooled to 0° C. in a freezer for 2 hours to facilitate precipitation of pyridinium chloride salt (PyCl). After 2 hours, the medium was filtered through a medium porous frit funnel and the filtrate was washed with 3–100 mL water washings. The organic layer was dried over Na2SO4 for 2 hours. The CH2Cl2 was stripped on a roto-evaporator to concentrate the CnGlyAdp. The material was purified by recrystallization (from 1:1 ethyl acetate/hexane). Yield of BnGlyAdp: 7.72g (64.0%). $_1$H NMR (d$_7$ DMF):δ 1.67 (s, 4H), 2.46 (s, 4H), 4.80 (s, 4H), 5.23 (s, 4H), 7.44 (m, 10H).

Preparation of 2,3-[(carboxymethyl)oxycarbonyl]octanoyloxyacetic acid (HOGlyAdp). Compound HOGlyAdp was synthesized by methods similar to those described for HOGlySuc, compound 4b, by dissolving BnGlyAdp (5.01 g, 11.3 mmoles) in 250 mL 2-proponal at room temperature in the presence of 1.51 g Pd/C (Degussa type). An air stone was immersed in the medium through rubber septum at the top of the flask. The medium was sparged with hydrogen gas at 1 atm. The system was isolated from air using a closed system bubbler. The medium was sparged with hydrogen gas for 12 hours. After 12 hours, the reaction mixture was filtered through celite to remove the catalyst and the reaction product was concentrated in vacuo resulting in a white solid. The white product was triturated with 1:1: diethyl ether/hexane. The white product was recovered by filtration through a medium porous filter funnel and then dried under vacuum in a desiccator. Yield of HOGlyAdp: 1.74 g (60.0%).

Preparation of di{1-methyl-2-(2-ethyl)oyloxycarbonyl}methyloctane-1,8-dioate (HEMAGlyAdp). Compound HEMAGlyAdp was synthesized by methods similar to those described for HPMAGlySuc, compound 5b. The cross-linker HEMAGlyAdp was prepared by adding HOGlyAdp (500 mg, 1.92 mmoles) and CDI (622 mg, 3.83 mmoles) to a 50 mL boiling flask. The flask was evacuated 3 times while iteratively purging with nitrogen. The temperature of the reaction vessel was reduced from room temperature to 0° C. with an ice bath and dry DMF (5 mL) was rapidly added to the vessel under pressure with vigorous stirring via a magnetic stir bar. Addition was accompanied with frothing and the formation of a white slurry, the intermediate precursor, the diimidazolide of GlyAdp. The slurry was allowed to come to room temperature and hydroxyethyl methacrylate (HEMA, 466 µL, 3.84 mmoles) was added via a syringe. The vessel was covered with aluminum foil to shield it from light and the reaction mixture was stirred under nitrogen atmosphere for 15 hours over which time the slurry completely dissolved. TLC of the reaction mixture showed the presence of both unreacted HEMA and HEMAGlyAdp (5.95 methanol/$CH_2Cl_2$ Rf=0.80). The reaction was diluted with 100 mL $CH_2Cl_2$ and washed with 1M $NaH_2PO_4$ (pH 4.5, 2–50 mL), 1M $NaHCO_3$ (pH 8.3, 2–50 mL) and brine (2–50 mL). The organic layer was dried over $Na_2SO_4$. The organic layer was recovered by filtration and solvent removed in vacuo (T<30° C.) yielding a yellow oil that was purified by flash chromatography on a SiO2 column (5 cm id by 30 cm) eluting with $CH_2Cl_2$. Fractions containing pure product were combined and the solvent was removed in vacuo (T<30° C.) yielding a colorless oil.

The following citations are incorporated in pertinent part by reference herein for the reasons cited in the above text.

References

Allcock, H. R., Polyphasphazines as new biomedical materials. Biodegradable polymers as drug delivery systems. M. Chasin and R. Langer. New York, N.Y., Marcel Decker. 45, 163 (1990).

Alfrey, T., Gurnee, E. F. & Lloyd, W. G., Diffusion in glassy polymers, J. Polymer. Sci. C, 12 (1966) 249.

Allcock, H. R., in Polyphasphazines as new biomedical materials, eds. Chasin, M. & Langer, R. (Marcel Decker, New York, N.Y.), Vol. 45, pp. 163 (1990).

Devices Tripartite Biocompatibility Guidance (FDA, Washington D.C.) 1987.

Baker, R. W. in Biodegradable Systems (John Wiley & Sons, New York, N.Y.), pp. 120 (1987).

Bender, M. L., Mechanisms of catalysis of nucleophilic reactions of carboxylic acid derivatives, Chem. Rev., 60 (1960) 53.

Burkoth, A. K., Anseth, K. S. "MALDI-TOF Characterization of Highly Cross-linked, Degradable Polymer Networks." Macromolecules, 32 (1999) 1438.

Brondsted, H. & Kopecek, J., Hydrogels for site-specific oral drug delivery: Synthesis and characterization, Biomaterials, 12 (1991) 584.

Chasin, M. & Langer R., Biodegradable polymers as drug delivery systems (Marcel Decker, New York, N.Y.) (1990).

Tripartite Subcommittee for Medical Devices, Tripartite Biocompatibility Guidance. (Washington D.C., FDA) (1987).

Drobnik, J. & Rypacek, F., Soluble synthetic polymers in biological systems, ed. Dusek, K. (Springer-Verlag, Berlin, UDR), 57 (1984) 30.

Duncan, R., Dimitrijevic, S. & Evagorou, E. G., Polymer therapeutics for tumor specific delivery, STP Pharma. Sci., 4 (1996) 237.

Eichenbaum, G., P. Kiser, et al., pH and Ion-Triggered Volume Response of Anionic Hydrogel Microspheres. Macromolecules 31 (1998) 5084.

Flory, P. J., Principles of Polymer Chemistry (Cornell University PRESS, Ithaca) (1953).

Heller, J., in Bioerodible Hydrogels, ed. Peppas, N. (CRC Press, Boca Raton), Vol. Volume III, pp. 137–148 (1986).

Heller, J., Sparer, R. V. & Zentner, G. M., in Poly(ortho-esters), eds. Chasin, M. & Langer, R. (Marcel Decker, New York, N.Y.), Vol. 45 (1990).

Heller, J., Controlled release of water soluble macromolecules from bioerodable hydrogels, Biomaterials. (1983) 262.

Isrealachvilli, J. (1991). Intersurface Forces. London, Academic Press.

Kenny, J. F. & Willcockson, G. W., Structure-property relationships of PVA. III. Relationships between stereoregularity, crystallinity, and water resistance in PVA, J. Polym. Sci, Al (1966).699.

Kiser, P. F., Needham, D. & Wilson, G., A synthetic mimic of the secretory granule for drug delivery, Nature, 394 (1998) 459.

Kreuter, J., Ed. Colloidal Drug Delivery Systems. Drugs and the pharmaceutical sciences. N.Y., Marcel Dekker (1994).

Kopecek, J. & Bazilova, H., Poly [N-(2-Hydroxypropyl) Methacrylamide]-I Radical polymerization and copolymerization, European Polymer Journal, 9 (1974) 7.

Kost, J. & Langer, R., in Equilibrium Swollen hydrogels in controlled release applications, ed. Peppas, N. (CRC Press, Boca Raton), Vol. 3, pp. 95–105 (1986).

Kurisawa, M., Matsuo, Y. & Yui, N., Modulated degradation of hydrogels with thermo-responsive network in relation to their swelling behavior, Macromol. Chem. Phys., 199 (1998) 707.

Lasic, D. D. and D. Needham, The Stealth liposome: a prototypical biomaterial." Chemical Reviews 95 (1995) 2601.

Lee, P., Kinetic considerations of drug delivery from swelling-controlled and erosion/diffusion-controlled systems, Proceed. Intern. Symp. Control. Rel. Bioact. Mat., 18 (1991) 315.

Mark, J. E., The use of model polymer networks to elucidate molecular aspects of rubberlike elasticity, Adv. Poly, Sci., 44 (1982) 1.

Munk, P. Introduction to macromolecular science (John Wiley & Sons, New York, N.Y.) (1989).

Odian, G., Principles of polymerization (John Wiley and Sons, N.Y.) (1991).

Park, K., Shalaby, W. S. W. & Park H., Biodegradable hydrogels for drug delivery (Technomic Publishing Co., Lancaster, Pa.) (1993).

Park, K., Biodegradable Hydrogels for Drug Delivery (Technomic Publishing Company, Inc., Lancaster, Pa.) (1993).

Pathak, C. P., Barman, S. P., Coury, A. J., Sawhney, A. S. & Hubbell, J. A., Biodegradable thermoresponsive hydrogels and macromonomers, Proc. Int. Symp. Controlled Release Bioact. Mater., 22 (1995) 85.

Peppas, N. A., Hydrogels in Medicine and Pharmacy, Volume II, Polymers (CRC Press, Boca Raton, Fla.) (1986).

Peppas, N., In Characterization of the Cross-linked Hydrogels, ed. Peppas, N. (CRC Press, Boca Raton), Vol. 1, pp. 27 (1986).

Peppas, N., In Dynamically swelling, hydrogels in controlled release applications, ed. Peppas, N. (CRC Press, Boca Raton), Vol. 3, pp. 109 (1986).

Rembaum, A., S. P. Yen, et al., Functional polymeric microspheres based on 2-hydroxyethyl methacrylate for immunochemical studies, Macromolecules, 9 (1976) 328.

Saffran, M., Kumar, G. S., Savarian, C., Burnham, J. C., Williams, F. & Necker, D. C., A New Approach to oral administration of insulin and other peptide drugs, Science, 233 (1986) 1081.

St. Pierre, T. & Chiellini, E., Biodegradability of medical polymers used in medical and pharmaceutical applications: Part 1-Principles of hydrolysis mechanisms, J. Bioact. Compatible Polym., 1 (1986) 467.

Subr, V., Duncan, R. & Kopecek, .J., Release of macromolecules and daunomycin from hydrophilic gels containing enzymatically degradable bonds, J. Biomater, Sc. Polym.Ed., 1 (1990) 261.

Taft, R. W., Polar and steric substituent constants for aliphatic and o-benzoate groups from rates of esterification and hydrolysis of esters, J. Amer. Chem. Soc., 74 (1952) 3120.

Taft, R. W., Linera free energy relationships from the rates of esterification and hydrolysis of aliphatic and ortho-substituted benzoate esters, J. Amer. Chem. Soc., 74 (1952) 2729.

Taylor, A. E. & Grainger, D. N., Exchange of macromolecules across the microcirculation, Handbook of Physiol., 6 (1984) 467–520.

Tomlinson, E., Theory and practice of site-specific drug delivery, Advanced Drug Delivery Reviews, 1(2) (1987) 87–198.

Torchilin, V. P., Tischenko, E. G., Smirnov, V. N. & Chazov, E. I., Immobilization of enzymes on slowly soluble carriers, J. Biome. Mat. Res., 11 (1977) 223.

Ulbrich, K., Subr, V., Seymour, L. W. & Duncan, R., Novel Biodegradable hydrogels prepared using the divinylic cross-linking agent N,0-dimethylacryloylhydroxylamine 1. Synthesis and characterization of rates of gel degradation, and rate of release of model drugs in vitro and in vivo., J. Controlled Release, 24 (1993) 181.

Van Dijk-Wolthius, W., Hoogeboom, J. A. M., van Steenbergen, M. J., Tsang, S. K. Y. & Hennink, W. E., Degradation and release behavior of dextran-based hydrogels, Macromolecules, 30 (1997) 4639.

Van Dijk-Wolthius, W. N. K., Tsang, S. K. Y., Kettees-van den Bosch, J. J. & Hennink, W. E., A new class of polymerizable dextrans with hydrolyzable groups: hydroxyethyl methacrylated dextran with and without oligolactate spacer, Polymer, 38 (1997) 6235.

Wang, P. Y. & Arlitt, B. P., in Structural requirements for the degradation of condensation polymers in vivo, ed. Gregor, H. P. (Plennum Press, New York, N.Y.), Ch. 16 (1975).

What is claimed:

1. A monomeric or oligomeric cross-linker comprising a polyacid with at least two acidic groups directly or indirectly being covalently connected to reactive groups usable to cross-link polymer filaments wherein between at least one reactive group and an acidic group of the polyacid is a biodegradable sequence consisting of a hydroxyalkyl acid ester sequence having a number of hydroxyalkyl acid ester groups selected from the group consisting of 1, 2, 3, 4, 5 and 6; the cross-linker being usable for crosslinking polymer filaments to form a network of cross-linked polymer filaments with a defined biodegradation rate.

2. The cross-linker of claim 1 wherein the polyacid is a polycarboxylic acid.

3. The cross-linker of claim 1 wherein a water soluble region is between at least one of said acidic groups and said reactive groups.

4. The cross-linker of claim 1 wherein the cross-linked polymer filaments are those of a hydrogel.

5. The cross-linker of claim 1 wherein the polymer filaments are hydrophobic.

6. The cross-linker of claim 1 wherein the polyacid comprises at least one acidic group attached to a water soluble region.

7. The cross-linker of claim 1 wherein the polyacid is a diacid.

8. The cross-linker of claim 1 wherein the polyacid is a triacid.

9. The cross-linker of claim 1 wherein the polyacid is a pentaacid or tetraacid.

10. The cross-linker of claim 1 wherein the polyacid is ethylenediaminetetraacetic acid (EDTA) or diethylenetriaminepentaacetic acid (DTPA).

11. The cross-linker of claim 1 wherein when polymer filaments are cross-linked, the biodegradable sequence contains at least two hydroxyalkyl acid ester groups.

12. The cross-linker of claim 1 wherein when polymer filaments are cross-linked, the biodegradable sequence contains one hydroxyalkyl acid ester group.

13. The cross-linker of claim 1 wherein the hydroxyalkyl acid ester sequence comprises an alpha hydroxyalkyl acid ester group.

14. The cross-linker of claim 1 wherein the biodegradable sequence comprises a hydroxyalkyl acid ester group selected from the group consisting of at least one of lactate and glycolate.

15. The cross-linker of claim 1 wherein the hydroxyalkyl acid ester sequence contains a hydroxyalkyl acid ester group selected from the group consisting of glycolic ester, DL-lactic acid ester, L-lactic acid ester, and combinations thereof.

16. The cross-linker of claim 1 further comprising at least one member selected from the group consisting of ethylene glycol oligomer, poly(ethylene) glycol, poly(ethylene oxide), poly(vinylpyrrolidone), poly(ethylene oxide)-co-poly(propylene oxide), and poly(ethyloxazoline).

17. The cross-linker of claim 1 wherein the reactive group contains a carbon-carbon double bond.

18. The cross-linker of claim 1 wherein the reactive group is an end group.

19. The cross-linker of claim 1 wherein the reactive group contains a carbonate, carbamate, hydrazone, hydrazine, cyclic ether, acid halide, acyl azide, succinimidyl ester, imidazolide or amino functionality.

20. The cross-linker of claim 1 wherein cross-linking of polymer filaments can be started by thermal, catalytic or photochemical initiation.

21. The cross-linker of claim 1 wherein cross-linking of polymer filaments can be initiated by pH change.

22. The cross-linker of claim 1 wherein crosslinking of polymer filaments can be by free radical addition or Michael addition.

23. The cross-linker of claim 1, or network of claim 25 wherein the polyacid has a molecular weight between 60 and 400 Da; the hydroxyalkyl acid ester sequence has a molecular weight between 70 and 500 Da and the reactive group has a molecular weight between 10 and 300 Da.

24. The cross-linker of claim 1 where the polyacid is selected from the group consisting of succinic acid, adipic acid, fumaric acid, maleic acid, sebacic acid, malonic acid, tartaric acid and citric acid.

25. A network of cross-linked polymer filaments with a defined biodegradation rate and cross-linked by a monomeric or oligomeric cross-linker comprising a polyacid with at least two acidic groups directly or indirectly covalently connected to reactive groups usable to cross-link polymer filaments wherein between at least one reactive group and an acidic group of the polyacid is a biodegradable sequence consisting of a hydroxyalkyl acid ester sequence having a number of hydroxyalkyl acid ester groups selected from the group consisting of 1, 2, 3, 4, 5 and 6.

26. A network of cross-linked polymer filaments with a defined biodegradation rate under in vivo mammalian conditions formed of preformed polymer filaments of polynucleic acids, polypeptides, proteins or carbohydrates and cross-linked by a monomeric or oligomeric cross-linker comprising a polyacid with at least two acidic groups directly or indirectly covalently connected to reactive groups usable to cross-link polymer filaments wherein between at least one reactive group and an acidic group of the polyacid is a biodegradable sequence consisting of a hydroxyalkyl acid ester sequence having a number of hydroxyalkyl acid ester groups selected from the group consisting of 1, 2, 3, 4, 5 and 6.

27. The network of claim 26 comprising biologically active molecules.

28. A network of cross-linked polymer filaments with a defined biodegradation rate under mammalian in vivo conditions, cross-linked by a monomeric or oligomeric cross-linker comprising a polyacid with at least two acidic groups directly or indirectly covalently connected to reactive groups usable to cross-link polymer filaments wherein between at least one reactive group and an acidic group of the polyacid is a biodegradable sequence consisting of a hydroxyalkyl acid ester sequence having a number of hydroxyalkyl acid ester groups selected from the group consisting of 1, 2, 3, 4, 5 and 6; said network comprising an organic molecule, inorganic molecule, protein, carbohydrate, poly(nucleic acid), cell, tissue or tissue aggregate.

29. A network of cross-linked polymer filaments with a defined biodegradation rate under mammalian in vivo conditions cross-linked by a monomeric or oligomeric cross-linker comprising a polyacid with at least two acidic groups directly or indirectly covalently connected to reactive groups usable to cross-link polymer filaments wherein between at least one reactive group and an acidic group of the polyacid is a biodegradable sequence consisting of a hydroxyalkyl acid ester sequence having a number of hydroxyalkyl acid ester groups selected from the group consisting of 1, 2, 3, 4, 5 and 6, and the network comprising an organic radioisotope, inorganic radioisotope or nuclear magnetic resonance relaxation reagent.

30. A microparticle or nanoparticle cross-linked polymer composition with a defined biodegradation rate under mammalian in vivo conditions and containing polymer filaments cross-linked by a monomeric or oligomeric cross-linker comprising a polyacid with at least two acidic groups directly or indirectly covalently connected to reactive groups usable to cross-link polymer filaments wherein between at least one reactive group and an acidic group of the polyacid is a biodegradable sequence consisting of a hydroxyalkyl acid ester sequence having a number of hydroxyalkyl acid ester groups selected from the group consisting of 1, 2, 3, 4, 5 and 6.

* * * * *